United States Patent [19]

Czaplewski et al.

[11] Patent Number: 5,965,697
[45] Date of Patent: Oct. 12, 1999

[54] DISAGGREGATED MUTANT HUMAN RANTES

[75] Inventors: Lloyd George Czaplewski; Michael George Hunter; Richard Mark Edwards; Keith Martyn Dawson, all of Oxford, United Kingdom

[73] Assignee: British Biotech Pharmaceuticals Limited, Oxford, United Kingdom

[21] Appl. No.: 08/936,387

[22] Filed: Sep. 25, 1997

Related U.S. Application Data

[60] Provisional application No. 60/026,920, Sep. 25, 1996.

[51] Int. Cl.⁶ .......................... C07K 14/52; C12N 15/19; C12N 15/63; C12N 5/10
[52] U.S. Cl. ........................ 530/324; 530/412; 435/69.5; 435/71.1; 435/71.2; 435/471; 435/325; 435/252.3; 435/320.1
[58] Field of Search ...................................... 530/351, 300, 530/324, 412; 435/69.5, 71.1, 71.2, 471, 325, 252.3, 320.1

[56] References Cited

FOREIGN PATENT DOCUMENTS

WO9313206  7/1993  WIPO .
WO9407521  4/1994  WIPO .

OTHER PUBLICATIONS

Schall Cytokine, 3:165–183, 1991.
Arenzana–Seisdedos et al., Nature 383:400, 1996.
Oppenheim. Ann. Rrev. Immunol., 9:617–648, 1991.
Schmidtmayerova et al., Nature 382:767, 1996.
Schall et al., J. Immunology, 141:1018–1025, 1988.
Meurer et al., J. Exp. Med. 178:1913–1921, 1993.
Taub et al., J. Leukocyte Biology, 59:81–89, 1996.
Bacon et al., Science 269:1727, 1995.
Ebisawa et al., J. Immunology, 153:2153–2160, 1994.
Bacon et al., J. Exp. Med. 184:873–882, 1996.
Rot et al., J. Exp. Med., 176:1489–1495, 1992.
Szabo et al., Eur. J. Immunol. 27:1061–1068, 1997.
Powell et al., European Resp. Journal 9(12):2454–2460, 1996.
Conklyn et al., Cytokine 8:762–766, 1996.
Alam et al., Am. J. Respir. Cell Mol. Biol. 7:427–433, 1992.
Combadiere et al., J. Leukocyte Biol. 60:147–152, 1996.
Kurashima et al., J. Leukocyte Biology 59:313–316, 1996.
Ben–Baruch et al., J. Biol. Chem. 270:22123–22128, 1995.
Robinson et al., Clin. Exp. Immuno 101:398–407, 1995.
Proudfoot et al., J. Biol. Chem. 271:2599–2603, 1996.
Godiska et al., J. Neuroimmunology 58:167–176, 1995.
Hoogewerf et al., Biochem. Biophys. Res. Comm. 218:337–343, 1996.
Khorram et al., Amer. J. Obs. Gyn. 169:1545–1549, 1993.
Neote et al., Blood 84:44–52, 1994.
Canque and Gluckman, Blood 84(10) Suppl 1:p480a, Abstract No. 1907, 1994.
Cocchi et al., Science 270:1811–1815, 1995.
Paxton et al., Nat Med 2:412–417, 1995.

*Primary Examiner*—Prema Mertz
*Attorney, Agent, or Firm*—Hale and Dorr LLP

[57] ABSTRACT

This invention relates to mutants of human RANTES (hRANTES) which, relative to the wild-type molecule, have a reduced tendency to aggregate into large multimeric complexes at physiological ionic strength and pH, and are less pro-inflammatory.

4 Claims, 17 Drawing Sheets

DISAGGREGATED MUTANT HUMAN RANTES

This invention claims priority to U.S. Provisional application Ser. No. 60/026,920, filed Sep. 25, 1996.

This invention relates to mutants of human RANTES (hRANTES) which, relative to the wild-type molecule, have a reduced tendency to aggregate into large multimeric complexes at physiological ionic strength and pH, and are less pro-inflammatory. This invention also relates to the use of such mutants in treating diseases mediated by overproduction of RANTES; to the use of such mutants, alone or in conjunction with other human immunodeficiency virus (HIV) inhibitors, for the treatment or prevention of HIV infection; to the use of such mutants as adjuvant molecules, and; to the use of such mutants as ligands in assay procedures used to identify molecules which bind to hRANTES receptors.

BACKGROUND TO THE INVENTION

Human RANTES (Regulated on Activation, Normal T Expressed and Secreted) is a pro-inflammatory cytokine that promotes cell accumulation and activation in chronic inflammatory diseases. It is a member of the chemokine superfamily (Schall. Cytokine. 3:165–183, 1991; Oppenheim. Ann. Rev. Immunol.9:617–648, 1991) and was originally cloned by Schall et al. (J. Immunology. 141:1018–1025,1988). hRANTES is composed of sixty eight amino acids. hRANTES shares considerable amino acid homology and indeed tertiary structural homology with hMIP-1α (LD78) and hMIP-1β (ACT-2).

The following papers describe some of the functions of hRANTES, such as chemotaxis, cellular activation, recruitment of cells to sites of inflammation etc.: Taub et al., J. Leukocyte Biology 59:81–89, 1996; Ebisawa et al., J. Immunology 153:2153–2160, 1994; Rot et al., J. Exp. Med. 176:1489–1495, 1992.

RANTES expression has been demonstrated in many diseases characterised by a mononuclear cell infiltrate, suggesting that RANTES may play a role in the generation of the inflammatory infiltrate. Particular diseases or conditions in which RANTES has been implicated include: transplant rejection (particularly renal allograft rejection and lung transplantation), atherosclerosis, arthritis (particularly osteo- and rheumatoid arthritis), atopic dermatitis, airway inflammatory disorders such as Rous Sarcoma Virus-induced bronchiolitis, delayed type hypersensitivity (DTH) reactions, glomerular nephritis, asthma, endometriosis and cancers (particularly T cell lymphomas, renal cell carcinoma and Wilms' tumours (Pattison et al., Clinical Immunother. 4(1):1–8, 1995). Pattison et al., (supra) reviews the biological activities of RANTES, its expression in various disease states, and therapeutic implications. RANTES has been identified as one of the agents, termed histamine release inhibitory factors, capable of inhibiting histamine release from mast cells and basophils and has therefore been proposed as a therapeutic agent in treating allergic or chronic inflammatory diseases (WO 94/07521). RANTES plays a key role where eosinophilic tissue infiltration represents a characteristic histopathological feature. For example, eosinophil-dominated inflammation is a hallmark of asthmatic airways, and it is believed that RANTES is involved in the mechanism of eosinophil recruitment to the asthmatic bronchial mucosa (Powell et al., European Resp. Journal. 9(12):2454–2460,1996).

When agonist molecules, such as hRANTES, are administered, it may be possible to desensitise the cells and paradoxically achieve an apparent antagonist effect. This phenomenon has been demonstrated with the related chemokine IL-8 (Hechtman et al., J. Immunol 147:883–892, 1991; Smith et al., Immunology 78:491–497, 1993). Alam et al., (Am. J. Respir. Cell Mol. Biol. 7:427–433, 1992) also demonstrated that both IL-8 and RANTES inhibited monocyte chemoattractant peptide-1- and histamine releasing factor-induced histamine release from basophils in a dose-dependent fashion at concentrations of $10^{-9}$ to $10^{-7}$ M.

The following papers describe some of the disease states in which hRANTES is implicated and represent potential targets for desensitisation therapy: Kurashima et al., J. Leukocyte Biology 59:313–316, 1996, for asthma; Robinson et al., Clin. Exp. Immuno 101:398–407, 1995, for rheumatoid arthritis; Godiska et al., J. Neuroimmunology 58:167–176, 1995, for multiple sclerosis and; Khorram et al., Amer. J. Obs. Gyn. 169:1545–1549, 1993, for endometriosis.

Human RANTES along with several other chemotactic cytokine molecules (chemokines) are known to be able to suppress HIV infection in in vitro systems (Canque and Gluckman. Blood 84(10) Suppl 1: p480$a$, Abstract No.1907, 1994; Cocchi et al., Science 270:1811–1815, 1995; Paxton et al., Nat Med 2:412–417, 1995). The chemokines described to date which have this HIV inhibitory activity are hMIP-1α, hMIP-1 β and hRANTES. hMIP-1α and hMIP-1β are also known as LD78 and ACT-2 respectively.

The mechanism whereby chemokines and hRANTES in particular suppress the infectivity of HIV has not been described in detail. At a gross level, it would appear that hRANTES binds to G-protein coupled receptors (GPCRs) that act as co-factors necessary for HIV infectivity and effectively block infectivity by doing so. Four chemokine receptors: Fusin (CXCR4), CCR2$b$, CCR3 and CCR5 have been shown to act as HIV-1 co-factor receptors (Deng et al., Nature 381:661–666; Dragic et al., Nature 381:667–674). Arenzana-Seisdedos et al. (Nature. 383:400, 1996) recently reported that an 8 amino acid N-terminally truncated analogue of human RANTES which has lost the normal RANTES chemotactic and leukocyte-activating properties but still retained high affinity for chemokine receptors, was still capable of inhibiting HIV infection, indicating that receptor signalling and cell activation is probably not required for the anti-HIV effect of RANTES, and that mere blockade of the receptor may be sufficient.

Schmidtmayerova et al. (Nature. 382:767, 1996) reported that in sharp contrast to the observed antiviral properties on T-cells, the three chemokines hMIP-1α, hMIP-1β and hRANTES (at 500 ng/ml) apparently stimulated HIV-1 replication in macrophages. This effect was reported to be dose dependent (although no data was presented). They conclude that administration of high levels of β-chemokines could actually be harmful by enhancing HIV-1 replication in macrophages and/or intensifying virus-induced inflammation.

In contrast to the majority of human chemokines, hMIP-1α, hMIP-1β and hRANTES have the tendency to aggregate into large multimeric complexes in physiological solution. Such multimeric complexes are large, estimated at many times (>12×) the mass of the monomeric protein as determined by sedimentation equilibration analyti ultracentrifugation (AUC).

Although hRANTES, hMIP-1α and hMIP-1β have been implicated as possible agents for use in HIV therapy and other disease therapies, they are difficult to manufacture because of their tendency to aggregate into large multimeric complexes in physiological solution. They are also difficult to formulate due to the heterogeneity within their solutions. Disaggregated mutants of these chemokine molecules would have the benefits of easier manufacture, more defined solution characteristics and improved, reproducible formulation. These benefits are therefore particularly relevant to the clinical use of these chemokines.

WO-A-9313206 teaches the construction of disaggregated mutants of stem cell inhibitory proteins such as LD78.

An additional problem associated with the clinical administration of RANTES relates to its pro-inflammatory properties. When administered at high concentrations such as at an injection site, inappropriate immune stimulation and inflammation can occur. A single intradermal injection of RANTES into dog skin resulted in a large, dose-dependent, eosinophil and macrophage-rich inflammatory site within 4 hours, providing evidence that RANTES has significant pro-inflammatory activity (Meurer et al. J. Exp. Med. 178:1913–1921, 1993). The inflammatory response was mild at low doses ($\leq 0.5$ $\mu$M hRANTES at the injection site) but led to full dermal thickening at higher doses ($\geq 1$ $\mu$M hRANTES at the injection site). In the context of using RANTES for therapeutic treatments, such inflammatory responses could amount to serious undesirable side-effects. There is a need therefore, for non- or less-inflammatory RANTES analogues, and particularly those that retain the native agonist properties.

hRANTES has been shown to act via two independent signal transduction pathways in T-cells (Bacon et al., Science 269:1727, 1995). The high affinity G-protein coupled receptor (GPCR) signalling pathway is typical of chemokines and acts at relatively low agonist concentrations eg. 50 nM hRANTES. The high affinity GPCR mediated hRANTES signalling provides all of the "usual" activities of hRANTES. These are the activities which may be demonstrated at low concentrations of hRANTES (<100 nM) and include chemotaxis of leucocytes, calcium mobilisation via the GPCR and suppression of HIV infection, although the latter may only require receptor binding and not signalling. The low affinity signalling pathway is via the tyrosine kinase (TK) activity of the T-cell receptor complex and is observed only at higher agonist concentrations, >>100 nM, eg 1 $\mu$M hRANTES. Activation of the T-cell receptor complex leads to proliferation of T-cells, induction of interleukin-2 (IL-2) expression (a pro-inflammatory cytokine) and induction of IL-2 receptor expression (Bacon et al., 1995 supra). These hRANTES-induced events are antigen independent and represent inappropriate immune stimulation. The low affinity T-cell receptor mediated signalling which causes T-cell activation and calcium mobilisation via the T-cell receptor TK is a pro-inflammatory event which may be linked to chronic inflammatory conditions and is therefore not desirable.

Bacon et al. further characterised the effects of 1 $\mu$M hRANTES on T-cell activation in subsequent publications (Bacon et al., J. Exp. Med 184:873–882, 1996, and Szabo et al., Eur. J. Immunol. 27:1061–1068, 1997). In these studies they showed that hRANTES induced the phosphorylation of many proteins which play a central role in the development of T-cell focal adhesions and T-cell activation. They also found that hRANTES induced the expression of cell surface adhesion molecules such as CD44, CD50 and CD28 via the tyrosine kinase signal transduction pathway. They summarised that hRANTES was a potent immune modulator, distinct from antigen, which was able to activate T-cells resulting in their proliferation and homotypic adhesion. They speculated that activation of lymphocytes by hRANTES may be an important factor in pathologies characterised by high concentrations of RANTES but lacking other obvious antigenic stimulation.

In Bacon et al., (1996) ibid and in Szabo et al., ibid., the tendency of hRANTES to aggregate was noted but considered irrelevant to T-cell activation and homotypic aggregation. Indeed the authors implied that only monomeric or dimeric hRANTES was active and that aggregation would reduce the concentration of hRANTES active on T-cells and lymphocytes.

In addition to T-cell/lymphocyte activation and homotypic aggregation, hRANTES also induces the expression of cell-surface adhesion molecules such as CD11$b$ (Conklyn et al., Cytokine 8:762–766, 1996). Conklyn et al. showed that hRANTES induced a dose-dependent elevation in CD11$b$ by monocytes, neutrophils and eosinophils in human whole blood. The elevation of CD11$b$ was observed at a threshold of $10^{-8}$ M to $10^{-7}$ M hRANTES, peaking at $10^{-6}$ M hRANTES in their assay system. These doses of hRANTES correlate with the findings of Bacon et al., (1 995; ibid) and Szabo et al., (ibid).

The study of chemokine-receptor interactions and in particular hRANTES-receptor interactions is in its infancy. However, four human cellular receptors, CCR1, CCR4, CCR5 and Duffy and one viral receptor, US28, which interact with hRANTES with relatively high affinity have been studied in some detail.

Chemokine-receptor interactions have generally been studied in two ways; 1) direct receptor binding via competitive displacement studies, and 2) signal transduction studies, with the best studies using a combination of the two approaches.

When chemokine-receptor interactions have been studied, both homologous and heterologous competition experiments have been used. A radiolabelled ligand can be used to investigate the relative affinity of several cold competing chemokines in a heterologous experiment. A preferred strategy is to perform homologous competition experiments where the radiolabelled and cold chemokines are the same.

The three chemokines MIP-1$\alpha$, MIP-1$\beta$ and RANTES are the primary ligands for the CCR5 receptor, and it is these chemokines which inhibit HIV-1 infection via the receptor (Cocchi et al., 1995, ibid). Of these, RANTES is the most potent inhibitor of HIV-1 infectivity in vitro. This observation alone suggests the importance of being able to investigate the homologous interaction of RANTES on the CCR5 receptor. Combadiere et al., (J. Leukocyte Biol. 60:147–152, 1996) who were one of the first to identify the monocytotropic HIV-1 co-factor receptor, CCR5, claim however, that it is not possible to demonstrate convincing homologous hRANTES receptor binding to CCR5. Indeed, it is recognised in the art that there are great difficulties with homologous hRANTES displacement studies. Ben-Baruch et al. (J. Biol. Chem. 270:22123–22128, 1995) described these difficulties using cell lines transfected with the CCR1 receptor. While the cell lines were suitable for MIP-1$\alpha$ homologous displacement studies, homologous hRANTES displacement was incomplete and biphasic. More than 30% of total counts bound could not be displaced by excess cold hRANTES and less than 70% of the total counts bound were specifically and reversibly bound to the receptor. They suggested that the problems were associated with the aggregation of hRANTES. Similar results with CCR1 receptors have been reported by others (Proudfoot et al., J. Biol. Chem. 271: 2599–2603, 1996). Similar incomplete displacement (>30% of bound counts were not displaceable) have also been found with homologous hRANTES-CCR4 binding experiments (Hoogewerf et al., (Biochem. Biophys. Res. Comm. 218:337–343, 1996), and with studies using the Duffy receptor (Neote et al., Blood 84:44–52, 1994).

The art recognises therefore, that there are problems with hRANTES homologous receptor binding studies. Use of a disaggregated RANTES molecule as a ligand in receptor binding studies may alleviate these problems.

BRIEF DESCRIPTION OF THE INVENTION

The inventors have prepared disaggregated mutants of hRANTES. These mutants retain the ability to inhibit HIV infection and surprisingly have reduced pro-inflammatory properties. These disaggregated hRANTES mutants are, preferably, potent agonists of the GPCR pathway but have substantially reduced activity via the TK pathway. The reduction in aggregation and pro-inflammatory properties relative to wild-type protein increases their clinical utility by enabling easier manufacture and formulation and reducing inflammatory side-effects such as at the site of injection. As these mutants still retain their chemotactic ability (a GPCR pathway stimulated event) they may also prove useful as adjuvants.

DETAILED DESCRIPTION OF THE INVENTION

According to a first aspect, the invention provides for a disaggregated mutant of the human RANTES (hRANTES) chemokine molecule, the mutant being substantially incapable at physiological ionic strength of forming a stable multimer greater than a dodecamer as determined by Sedimentation Equilibrium Analytical Ultracentrifugation (AUC).

In a preferred embodiment of the invention the disaggregated RANTES mutants are less pro-inflammatory than wild-type hRANTES.

Aggregation is defined herein as the tendency, at 0.5 mg/ml in physiological solution, to exist with an average molecular weight in excess of 12× the molecular weight of the monomeric unit. This mass corresponds to greater than a dodecamer. In practice, as shown in the examples herein, hRANTES has such a great tendency to aggregate that the estimate of its aggregation has to be performed at a lower concentration for accurate data (0.1 mg/ml). Even at this lower concentration the average molecular weight of native hRANTES is still greater than a dodecamer of hRANTES monomers. Due to the concentration dependency of the aggregation of chemokines, estimation of the average molecular weight of hRANTES at 0.1 mg/ml will underestimate the average molecular weight at 0.5 mg/ml.

By the term "disaggregated mutant" as used herein is meant a molecule differing in amino acid sequence from a natural (wild-type) RANTES protein (such as that depicted in SEQ ID No. 1), yet derived from such a sequence by mutagenesis, which at physiological ionic strength and at 0.5 mg/ml is substantially incapable of forming multimers higher than a dodecamer as determined by analytical ultracentrifugation (AUC).

It is preferred that the number of amino acid changes from the natural protein, such as that depicted in SEQ ID No. 1, necessary to create the disaggregated mutant is no more than 10, and preferably in increasing order of preference 8, 7, 6, 5, 4, 3, 2 and 1.

Such analogues could be derived from the natural protein depicted in SEQ ID No. 1, or any other natural RANTES allelic protein, by deletion, addition or substitution of one or more amino acid residues. As a practical matter the disaggregated hRANTES mutants of the invention will possess a high degree of amino acid homology, or amino acid sequence identity, with the wild-type protein. It will be realised that the nature of the changes from the wild-type molecule is more important than the number of changes. As guidance, though, at the amino acid level, it may be that in increasing order of preference, at least 58, 60, 61, 62, 63, 64, 65, 66 or 67 of the residues will be the same as the native prototype molecule. At the nucleic acid level, nucleic acid coding for a disaggregated mutant (analogue) will hybridise under stringent conditions (such as at approximately 40° to 65° C. in a salt solution of approximately 0.9 molar) to nucleic acid coding for the native prototype molecule, or would do so but for the degeneracy of the genetic code.

The amino acid sequence of human RANTES depicted in SEQ ID No. 1 represents the sequence isolated by Schall et al. (ibid). This protein has been isolated from one cell type from one human source. It will be appreciated that other isotypes/alleles of human RANTES may exist. It is likely that such alleles will differ from the amino acid sequence depicted in SEQ ID NO. 1 by no more than 10 amino acids. The instant invention is equally applicable to other natural isotypes/alleles of human RANTES that aggregate in physiological solution, and therefore, natural isotypes/alleles of human RANTES which differ from the amino acid sequence depicted in SEQ ID No. 1 by no more than 10 amino acids, and which isotype/allele aggregates at physiological ionic strength, are included in the definition of a human RANTES protein, and can be mutated to generate a disaggregated mutant according to the invention.

Throughout this specification, the words analogue, mutant and variant are used interchangeably. The words wild-type, native and natural are also used interchangeably.

The terms "physiological solution" or "physiological ionic strength" are well known to those skilled in the art. They are generally equivalent to about 137 mM NaCl, 3 mM KCl and about 1 mM phosphate. Physiological pH is about 7.4.

In a preferred embodiment of the invention, the disaggregated hRANTES mutant exists in physiological solution as a substantially homogeneous population of monomers, of dimers, of tetramers or of dodecamers as determined by AUC. It should be understood that a minor proportion of higher and/or lower order multimers is likely, from a consideration of thermodynamic equilibria, to exist within a substantially homogeneous population of any given multimeric state. The population is considered substantially homogeneous if a 0.5 mg/ml sample of mutant protein in physiological solution possesses less than 20%, preferably less than 15%, more preferably 10% or less of any other multimer formation as determined by AUC.

The sedimentation equilibration AUC method is known in the art (Varley et al., Eur. Biophys J. 25:437–443, 1997). In brief, it involves centrifuging the test sample until it reaches equilibrium, then determining the distribution of the sample across the sample tube by measuring the absorbance at an appropriate wavelength. From the resulting distribution the average molecular weight is estimated. A suitable protocol is described in Example 1(e) herein.

The inventors have made substitution mutations at Glu26 and Glu66. Example I herein, describes the construction of the disaggregated hRANTES mutants E26>A, E66>S and the double mutant E26>A+E66>S, and demonstrates that these analogues are, relative to the wild-type molecule, substantially disaggregated. Structural analysis of hRANTES indicates that substitution mutations at any of the following residues: Ser1, Pro18, His23, Glu26, Asn46, Asn52, Lys55, Glu60, Ser64, Glu66 and Met67 would also result is suitably disaggregated RANTES analogues. By following the teaching herein, other disaggregated hRANTES analogues with substitutions at these or other residues can be made.

Preferred disaggregated RANTES mutants of the invention comprise a substitution mutation at one or more of the amino acid residues with respect to wild-type RANTES selected from the group consisting of: Ser1, Pro18, His23, Glu26, Asn46, Asn52, Lys55, Glu60, Ser64, Glu66 and Met67. More preferred, are disaggregated hRANTES mutants of the invention that have either or both of the residues at positions 26 and 66 with respect to wild-type hRANTES substituted by other residues. The E26>A and E66>S substitutions being particularly preferred.

As used herein, nomenclature such as: E26>A, refers to the wild-type molecule wherein the glutamic acid residue at position 26 has been substituted by an alanine residue.

Alternatively, and by routine experimentation, one skilled in the art can randomly substitute one or more of the wild-type RANTES amino acids for different amino acids, preferably not conservative substitution changes, and test those analogues for their multimerisation state and their inability to induce pro-inflammatory responses. Amino acid deletion or addition mutations can similarly be made and tested by the person skilled in the art. As RANTES is encoded by a relatively small gene, the number of mutations that would have to be made and tested before a suitable disaggregated less pro-inflammatory RANTES analogue was found is limited, would not involve any undue experimentation or necessitate any inventive input and thus, would be well within the capabilities of the person skilled in the art.

The disaggregated RANTES mutants in accordance with the invention can in principle be made by any convenient means including chemical modification of existing (natural) proteins and/or chemical coupling of two or more oligo- or poly-peptide chains. The preferred methodology however, is to use recombinant DNA technology, which enables successive amino acids to be coupled together in vivo.

According to a further aspect of the invention there is provided nucleic acid coding for a disaggregated RANTES protein of the invention. Both DNA and RNA are within the scope of the invention. Nucleic acid in accordance with the invention can be prepared by any convenient means involving coupling together successive nucleotides, and/or ligating oligo- or poly-nucleotides, including in vitro processes, but recombinant technology forms the method of choice.

Mutations may be introduced by de novo polynucleotide synyhesis, by site-directed mutagenesis using appropriately designed oligonucleotide primers or by any other convenient means known to the person skilled in the art.

Recombinant DNA in accordance with the invention may be in the form of a vector. The vector may for example be a plasmid, cosmid or phage. Vectors will usually contain one or more selectable markers to enable selection of host cells transformed/transfected with the vector. Appropriate translational initiation and termination signals will generally be present. Additionally, if the vector is intended for expression, appropriate transcriptional regulatory sequences and promoters to drive expression will be included.

The vectors containing the DNA coding for the disaggregated RANTES proteins according to the invention can be introduced into *E. coli*, or any other suitable hosts to facilitate their manipulation. Expression vectors may be adapted for prokaryotic expression but for preference are adapted for expression in microbial eukaryotic host cells, such as yeast (including but not limited to *Saccharomyces cerevisiae* and *Pichia pastoris*) or higher eukaryotic cells such as insect or mammalian cells.

Performance of the invention is neither dependent on nor limited to any particular strain of host cell or vector: those suitable for use in the invention will be apparent to the person skilled in the art.

According to a further aspect of the invention there is provided a host cell adapted to express a disaggregated RANTES mutant of the invention. The yeast *S. cerevisiae* is the preferred cell of choice.

Although RANTES has been implicated as a potential therapeutic agent in treating various inflammatory diseases, it is nevertheless a pro-inflammatory cytokine. Meurer et al. (J. Exp. Med. 178:1913–1921, 1992) demonstrated that subcutaneous injection of human RANTES into the beagle dog induces the formation of eosinophilic and monocytic intradermal inflammatory sites. In the context of using RANTES for therapeutic treatments, such inflammatory responses could amount to serious undesirable side-effects.

The term "pro-inflammatory" refers to the response of cells to a stimulus like hRANTES. The cells can respond to the stimulus in a number of ways for example, they could activate the T-cell receptor tyrosine kinase causing the mobilisation of calcium; initiate the secretion of cytokines eg. IL-2, IL-5, IL-6 or TNF-alpha; upregulate cytokine receptor expression eg. IL-2 receptors; release histamine or initiate proliferation. In vivo, the effect of these responses is to cause inflammation. Inflammation in tissues, which can present itself as redness and swelling may lead to tissue damage and chronic disease. Another term to describe the effects of hRANTES would be "lymphocyte activating". These two terms are used interchangeably throughout this specification.

The inventors have surprisingly found that disaggregated hRANTES mutant proteins in accordance with the invention are less pro-inflammatory or lymphocyte activating than the wild-type hRANTES protein in a calcium mobilisation assay using the Jurkat cell line, a surrogate assay for T-cell activation (Example 3). These findings have also been confirmed by measuring expression levels of various cell surface markers, such as the integrins, whose expression is linked to, or caused by T cell activation (Example 4). This discovery is surprising because it is contrary to that in the art, such as that described by Bacon et al. (1995, ibid) and Szabo et al. (ibid) who considered, but rejected, a link between hRANTES aggregation and its pro-inflammatory properties. In addition, the inventors have found that the more disaggregated (de-multimerised) the hRANTES analogue is, the less it induces a response on the protein tyrosine kinase pathway. It will be appreciated therefore, that disaggregated hRANTES mutants of the invention that exist substantially in monomeric form are preferred over those that exist substantially in dimeric form, which in turn are preferred over those that exist substantially in tetrameric form, which in turn are preferred over those that exist substantially in dodecameric form.

For the purpose of this specification, a molecule is less pro-inflammatory than wild-type when it mobilises less calcium than the wild-type molecule as measured in the calcium mobilisation assay described in Bacon et al. (Science 269:1727, 1995) and Example 3 described herein, on CD3+ Jurkat cells. In increasing order of preference, a less pro-inflammatory protein will mobilise less than 90%, 80%, 50%, 40%, 30%, 20%, 10%, 5%, 2%, and 1% of the amount of calcium mobilised by the same amount of wild-type hRANTES. Values for assessing whether or not a mutant RANTES is less pro-inflammatory should be the average from at least 2 repeat experiments. Less pro-inflammatory forms of hRANTES are beneficial for clinical administration, providing a reduction in the likelihood or severity of side effects or inappropriate immune stimulation, such as at the site of injection of a pharmaceutical preparation comprising concentrated exogenous disaggregated hRANTES. They allow the administration of hRANTES to humans, in cases where the wild-type molecule is too toxic, and allow higher dosage to be used than can safely be achieved with the wild-type hRANTES.

The inventors have also found that addition of disaggregated RANTES to cultured human T-lymphocytes was able to diminish the activation of the cells induced by wild-type hRANTES, demonstrating that disaggregated hRANTES antagonises hRANTES induced T-cell activation (Example 5). This discovery suggests that the disaggregated variants of hRANTES may not just be less pro-inflammatory or lymphocyte activating than wild-type hRANTES, they may actually be anti-inflammatory analogues of hRANTES.

Disaggregated RANTES analogues that lack the T-cell activation (pro-inflammatory response) activity via the tyrosine kinase pathway, whilst retaining the ability to chemoattract T lymphocytes, particularly of the memory type, are particularly suitable for use as adjuvants.

The in vivo consequence of the administration of wild-type hRANTES as an adjuvant would be to attract T-cells, monocytes, eosinophils etc. but that they, and particularly the T-cells, would be activated by the wild;PRANTES leading to their inappropriate antigen-independent proliferation and the production of a pro-inflammatory cytokine/chemokine response. Wild-type hRANTES may also induce activation-induced cell death (AICD) of the recruited T cells if local antigen presentation is not optimal. Local and recruited APCs may be deleteriously affected either directly by hRANTES or by the non-specific T cell activation.

The disaggregated hRANTES analogues which retain their chemoattractant activity (Example 2b) would however, be effective in vivo adjuvants by attracting immune cells to the site of administration but would be ineffective or substantially ineffective at activating T-cells once they arrived. The T-cells would, therefore, not be activated and driven into inappropriate proliferation or possibly cell death and would be available to interact correctly with antigen-presenting cells to deliver an augmented antigen-dependent immune response.

According to another aspect of the invention there is provided the use of a disaggregated RANTES analogue as an adjuvant.

For use as an adjuvant any antigen of interest can be co-administered with the disaggregated RANTES analogue. A person skilled in the art of adjuvant technology will be capable of preparing antigen:adjuvant formulations using the disaggregated RANTES analogues of the invention.

The teaching herein, enables one skilled in the art to assess whether the disaggregated hRANTES analogues have altered GPCR pathway versus TK pathway activity. The most preferred analogues will possess less activity at the TK pathway and therefore the greatest ratio of GPCR/TK activity.

In a preferred embodiment, the disaggregated RANTES analogue according to the invention is incapable, or substantially incapable (by which is meant less capable than wild-type RANTES), of T-cell activation, but still retains at least some affinity for binding the G-protein coupled receptor (GPCR). The analogue once bound to the receptor may induce signalling via the GPCR pathway, or alternatively it may act as an antagonist.

The less pro-inflammatory disaggregated hRANTES mutants of the invention may be used to cause desensitisation of cells. The ability of endogenous chemokine expression or exogenous chemokine administration to induce a non-responsive (or desensitised) state in normally responsive cells is well known. Administration of hRANTES could desensitise cells from responding to endogenously produced hRANTES but the pro-inflammatory nature of hRANTES may restrict the dosage, method of administration and/or its utility because of the side effects of inappropriate T-cell activation. The disaggregated forms of hRANTES would not suffer these drawbacks. In these circumstances, the disaggregated hRANTES would not only be efficacious as a suppressor of HIV infection, but would also act as an antagonist of all of the other functions of hRANTES, such as chemotaxis, cellular activation, recruitment of cells to sites of inflammation etc. that are described in the literature.

RANTES has been shown to bind the following chemokine receptors: CCR1, CCR3, CCR4, CCR5, US28 and DARC (see Howard et al. TIBTECH. 14:46–51, 1996). Various other chemokine molecules such as MIP-1α, MCP-1β MCP-2, MCP-3, GRO-α and IL-8 also bind and act through one or more of these same receptors. As demonstrated by Gong et al. (ibid) RANTES is capable of competing for the binding of certain other chemokines and inhibits their activity. The disaggregated RANTES analogues of the invention may therefore also prove useful in desensitising cells against the activities of those chemokines which bind and act through the same receptors as RANTES and thus may prove useful in treating diseases mediated by these other chemokines.

The art has described various RANTES analogues such as N-terminally deleted hRANTES analogues and hRANTES analogues which have been modified by chemical treatment (eg. addition of N-terminal amino-oxy-pentane) which are GPCR antagonists (eg. Arenzana-Seisdedos et al., Nature 383:400–400, 1996; Simmons et al., Science 276:276–279, 1997). If these analogues aggregate, as discussed above, it is likely that they will activate T-cells via the TK pathway and be pro-inflammatory. The introduction of disaggregating substitutions or modifications would reduce this pro-inflammatory property. The teaching of the instant invention is therefore equally applicable to the generation of disaggregated forms of aggregating RANTES analogues.

It is known in the art of chemokine biology that the composition and in particular the length of the N-terminus of the protein can have profound implications on the activity of chemokines. The prime examples of this are the activities of the various lengths of IL-8 (Padrines et al., FEBS Letters 353: 231–235, 1994). As defined herein, the serine residue at position 1, as depicted in SEQ ID No. 1, represents the N-terminal residue of wild-type hRANTES. hRANTES variants with altered N-terminal lengths are judged relative to this residue. Disaggregated hRANTES variants with altered N-terminal compositions and/or lengths are included in this invention. An example of a hRANTES analogue with an altered N-terminus is met-RANTES, possessing a methionyl residue preceding the serine at position 1 of SEQ ID No.1 (Proudfoot et al., J. Biol. Chem. 271:2599–2603, 1996). The addition of the methionine residue confers a degree of antagonistic activity upon the molecule which has proven useful in animals models of inflammation where it reduced the severity of symptoms (Platerzyberk et al., Immunology Letters 57,117–120, 1997). Although it is generally desirable for the analogues to retain their ability to bind to GPCRs there is a special case envisaged where the analogue may have lost this ability. A disaggregated hRANTES analogue which no longer binds to GPCRs may have utility as a potent and specific antagonist of hRANTES induced T-cell activation via the TK pathway and may have utility in the treatment of acute and chronic inflammatory conditions and in the suppression of transplant rejection.

As outlined in the "Background to the Invention", RANTES has been implicated in numerous inflammatory diseases and conditions including: transplant rejection (particularly renal allograft rejection and lung transplantation), atherosclerosis, arthritis (particularly osteo- and rheumatoid-arthritis), atopic dermatitis, airway inflammatory disorders such as Rous Sarcoma Virus-induced bronchiolitis, delayed type hypersensitivity (DTH) reactions, glomerular nephritis, asthma, endometriosis and cancers (particularly T cell lymphomas, renal cell carcinoma and Wilms' tumours). The ability to block the action of the native endogenous pro-inflammatory molecule in individuals by administering a less or non pro-inflammatory molecule, such as the molecules of the invention, may therefore be of particular therapeutic benefit to those patients suffering from these diseases or conditions.

According to a further aspect of the invention, there is provided for a pharmaceutical compositions comprising a disaggregated hRANTES mutant of the invention in combination with one or more pharmaceutically acceptable carriers or excipients. In particular, there is provided a pharmaceutical composition for the treatment of allergic or inflammatory diseases, and a method for the treatment of an inflammatory disease comprising administering to an individual a pharmaceutical composition comprising a therapeutically effective concentration of a disaggregated RANTES mutant protein in a pharmaceutically acceptable carrier.

The finding that inhibition of HIV by chemokines (eg, hMIP-1α, hRANTES and hMIP-1β) is dependent on their binding to G-protein coupled receptors (GPCRs) that act as co-factors necessary for HIV infectivity, has prompted a search for chemokine antagonists capable of inhibiting the binding of HIV, particularly the binding of the HIV protein gp120, to these GPCRs. One approach to the identification of these antagonists is to search for chemicals or biologicals able to block the binding of chemokines to the GPCRs and then assessing whether these molecules also blocks HIV binding. When screening for antagonists, it is desirable to use ligands with high affinity.

Because the RANTES analogues of the invention are substantially incapable of multimerising once bound to its cognate receptor, the disaggregated RANTES analogues of the invention should be more potent in homologous hRANTES receptor binding assays.

The inventors have also found that while wild-type hRANTES binds and interacts with proteoglycan molecules, such as glycosaminoglycan, on the cell surface, disaggregated hRANTES eg. hRANTES E66>S binds more effectively to proteoglycan molecules.

There is a desire and need in the art to develop assay methods for measuring proteoglycan ligand interactions and methods for identifying molecules which antagonise proteoglycan:ligand interactions.

The finding that the disaggregated RANTES analogues of the invention not only bind proteoglycan, as does wild-type hRANTES, but that labelled proteoglycan-bound disaggregated RANTES can be effectively displaced by cold disaggregated RANTES, promulgates the disaggregated RANTES analogues of the invention as tools for use in measuring proteoglycan:ligand interactions and as tools in assays developed for identifying molecules which can displace or antagonise the proteoglycan:ligand interaction.

In homologous RANTES receptor binding studies therefore, it would appear that wild-type human RANTES binds to its cognate receptor on the cell surface, to proteoglycan molecules on the cell surface, and because of its multimerisation property, to other RANTES molecules that are bound on the receptor or proteoglycans. It is probably because of this promiscuous or additional binding that wild-type RANTES is particularly poor in hRANTES receptor binding assays, and thus is poor for use in identifying molecules capable of interaction, i.e. antagonising, with RANTES bound on the receptor.

The disaggregated RANTES mutants of the invention should therefore be useful in receptor binding studies, particularly for use in screening compounds for their ability to interact with the RANTES receptors (i.e. chemokine receptors) or proteoglycans.

According to a further aspect of the invention there is provided for the use of a disaggregated RANTES analogue of the invention in an assay to determine RANTES:ligand interaction(s). The preferred ligand for the disaggregated RANTES being either a RANTES receptor or a proteoglycan molecule.

According to a further aspect of the invention there is provided for the use of a disaggregated RANTES analogue according to the invention in an assay to identify molecules which antagonise the RANTES:ligand interaction. This is preferably done by testing a compound (chemical or biological) for its ability to displace the disaggregated RANTES from the ligand. Again, the preferred ligand for the disaggregated RANTES being either a RANTES receptor or a proteoglycan molecule. In such assays, it is preferred that a detectable label is attached to the disaggregated RANTES analogue so as to enable accurate assessment of the degree of interaction with the proteoglycan or the degree of displacement by the antagonist molecule. Radioactive isotopes, such as iodine-125, or fluorescent tags or labels are particularly suitable and are known to those skilled in the art. The person skilled in the art would have no difficulty in developing a suitable competitive displacement assay using a labelled disaggregated RANTES analogue and a suitable mammalian cell line or cell preparation comprising either proteoglycan molecules and/or RANTES receptor molecules for use in screening a compound or compounds for their ability to displace the labelled analogue.

The minimum requirements for establishing a cell-based assay system for determining RANTES:ligand interactions or for identifying compounds that antagonise or competitively displace RANTES from its ligand are (i) a suitably labelled disaggregated RANTES mutant according to the invention, and (ii) a membrane preparation or mammalian host cell or cell line. The membrane preparation, the host cell or cell line capable of, or having been adapted to, express proteoglycan molecules and/or hRANTES receptors to which the labelled disaggregated RANTES mutant can bind.

The invention also provides for a method for screening a test compound for its ability to compete with RANTES on a RANTES receptor or on cell surface proteoglycans, consisting of:

(i) incubating for a suitable period, mammalian host cells or membrane preparations, that express RANTES receptors and/or proteoglycan molecules, with a labelled disaggregated RANTES mutant, and various concentrations of test compound; and (ii) determining the ability of the test compound to displace the labelled disaggregated RANTES bound to the proteoglycan and/or RANTES receptors.

When testing compounds for their ability to compete with the disaggregated RANTES analogue bound to a suitable RANTES receptor, because RANTES is now known to bind to proteoglycans on the cell surface, it is preferred that the assay utilises cells or cell membranes that lack proteoglycans. The suitable proteoglycan deficient cell line is the CHO cell line pgsA-745.

The less pro-inflammatory disaggregated RANTES analogues of the invention have been shown to inhibit HIV in vitro (Example 8).

According to another aspect of the invention, there is provided the use of a disaggregated mutant of the hRANTES chemokine molecule, in the preparation of a medicament for the treatment or prevention of HIV infection.

The use of the terms "human immunodeficiency virus" or "HIV" includes any member of the retroviral family eg HTLV-1, HTLV-2, HTLV-III (HIV-1) or HIV-2, but preferably refers to HIV-1.

The invention also provides the use of a disaggregated mutant of the hRANTES chemokine in conjunction with one or more other human immunodeficiency virus (HIV) inhibitors in the preparation of a medicament for separate, sequential or simultaneous use in the treatment or prevention of HIV infection.

Suitable HIV inhibitors for use in conjunction with the disaggregated hRANTES mutants of the invention in the preparation of a medicament for separate, sequential or simultaneous use in the treatment or prevention of HIV infection, are selected from the group consisting of: LD78, both wild-type and disaggregated mutants thereof; ACT-2, both wild-type and disaggregated mutants thereof; and non-proteinaceous inhibitory molecules.

The invention also provides a method of treating an HIV infected patient or one suspected of recent HIV infection, which comprises administering to the patient an amount of a disaggregated mutant of hRANTES effective in reducing the HIV burden of the patient.

The invention also provides for a method of prophylactic prevention of an HIV infection, comprising administering to a patient an HIV-inhibitory dose of disaggregated RANTES analogue.

The invention also provides for a method of prophylactic treatment of an HIV infection, comprising administering to a patient a dose of disaggregated RANTES analogue and one or more other human immunodeficiency virus (HIV) inhibitors effective to prevent HIV infection.

This invention also relates to the use of disaggregated mutants of the hRANTES chemokine molecule, alone or in conjunction with other known human immunodeficiency virus (HIV) inhibitors for the treatment of HIV infection.

The invention also includes a method of treating an HIV infected patient or one suspected of recent HIV infection, which comprises the simultaneous, separate or sequential administration of effective amounts of a disaggregated hRANTES molecule, and one or more HIV inhibitor molecules selected from the group consisting of: hMIP-1alpha (LD78), hMIP-1beta (ACT-2) and non-proteinaceous inhibitory molecules, together with a pharmaceutically acceptable carrier. Analogues and particularly disaggregated mutant forms of hMIP-1 alpha or hMIP-1 beta are included in the group.

Suitable non-proteinaceous inhibitory molecules which may be used in conjunction with the disaggregated hRANTES analogues include but are not limited to: HIV protease inhibitors such as ritonavir and indinavir or reverse transcriptase inhibitors such as AZT, or 3TC.

Chemokine molecules including disaggregated mutants thereof, such as hMIP-1α and hMIP-1β which are known to suppress the infectivity of HIV, the causative agent of the acquired immuno-deficiency syndrome (AIDS), may be co-administered with a disaggregated hRANTES mutant, to an HIV infected patient, or can be used in conjunction with the disaggregated hRANTES mutant in the preparation of a medicament for the treatment of HIV infection.

The use of disaggregated LD78 analogues in the treatment or prevention of HIV infection is disclosed in WO-A-97/25350.

Dosage of the agent(s) in accordance with any aspect of the invention will be such as is accepted to be effective following the clinical trials approved for that purpose by the relevant health regulatory authorities, and will be under the control of the physician or clinician considering various factors such as the condition, sex, weight of the patient and the degree or severity of any ailment.

Dosage of the disaggregated hRANTES analogues are expected to be from 1 µg/kg body weight to 10 mg/kg body weight and preferably between 1 µg/kg body weight and 1 mg/kg body weight. The amount, formulation and route of administration should be chosen to achieve an effective level of hRANTES analogue which is expected to be in the range of 50 µg/ml to 1 µg/ml circulating in blood or other target tissue.

Administration of the agent(s) can be by injection, preferably via intra-venous, intra-peritoneal, intra-muscular or sub-cutaneous routes. Other routes such as transdermal, oral, intranasal or by inhalation may also be possible. As with any treatment for inflammatory or allergic diseases such as asthma, the effective dosage should be adapted to meet the individual patient's needs, and raised or lowered depending on their propensity to develop acute episodes.

Oral dosages should be 5 to 100 times greater than the dosage for injection. For inhalation, which is the method of choice for respiratory allergic or inflammatory diseases such as asthma, rhinitis and brochiolitis, the specific disaggregated RANTES protein is solubilised and administered via an atomiser, nebuliser, aerosol dispenser or other suitable apparatus. The disaggregated RANTES protein can also be mixed with a suitable pharmaceutical carrier or diluent, e.g. saline. Dosages for a therapeutically effective amount for inhalation may range from 10 ng to 1 mg, preferably 100 ng to 100 µg, per inhalation. For topical administration, e.g. for atopic dermatitis and other skin inflammatory disorders, a therapeutically effective amount of the disaggregated RANTES protein can be formulated in a pharmaceutically acceptable carrier, such as a gel, liquid, lotion, cream, ointment, paste or powder. The range of excipients used in these can be chosen from those well known in the art to either maximise solubility of the product or to stabilise the active product with respect to chemical and physical characteristics. The dosage for topical administration will of course depend on the size of the area being treated. The concentration of the active ingredient in the topical formulation will usually be in the range of 0.01–3%, more preferably 0.1 to 1%.

In support of the invention, the invention shall be further described by way of the following figures and non-limiting examples which describe the construction of the disaggregated hRANTES mutants E26>A, E66>S and the double mutant E26>A+E66>S; the demonstration of the ability of the disaggregated hRANTES mutants to suppress HIV infection; the demonstration of the reduced ability of disaggregated hRANTES mutants to activate the TK pathway as demonstrated by calcium mobilisation in the Jurkat cell calcium mobilisation assay and cell surface expression of integrin molecules, when compared to wild-type hRANTES; and, the demonstration of the improvement in using a disaggregated RANTES mutant in cell-based competitive receptor-ligand displacement assays, compared to wild-type hRANTES.

Key: ●—wild-type RANTES; ▲—E26>A RANTES mutant; ○—E66>S RANTES mutant and E26>A+E66>S RANTES mutant.

Figure 11:
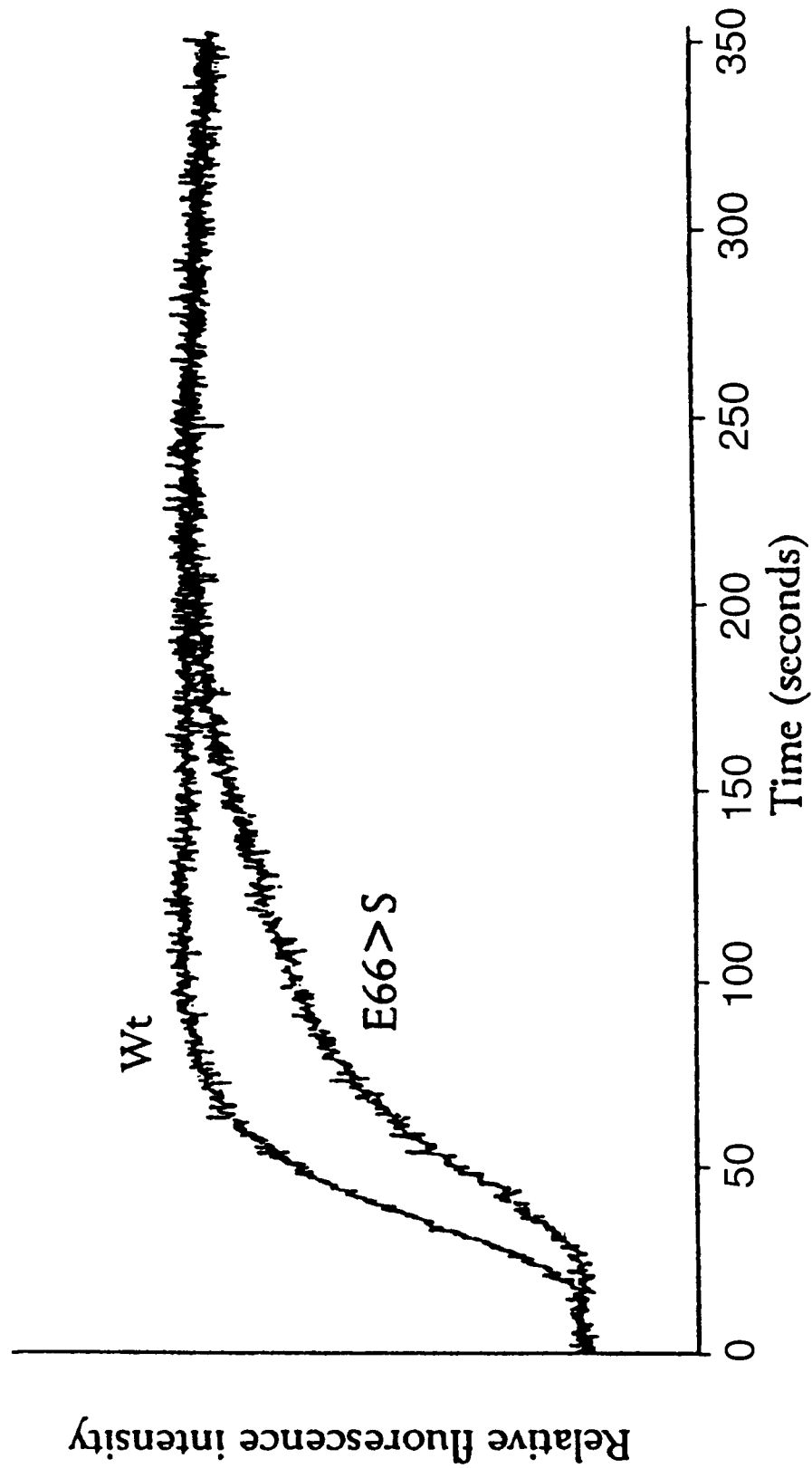

FIG. 11—Illustrates the calcium mobilisation response on Jurkat cells following administration of 2.5 μM wild-type RANTES, and 500 μM E66>S disaggregated RANTES mutant.

Figure 12:
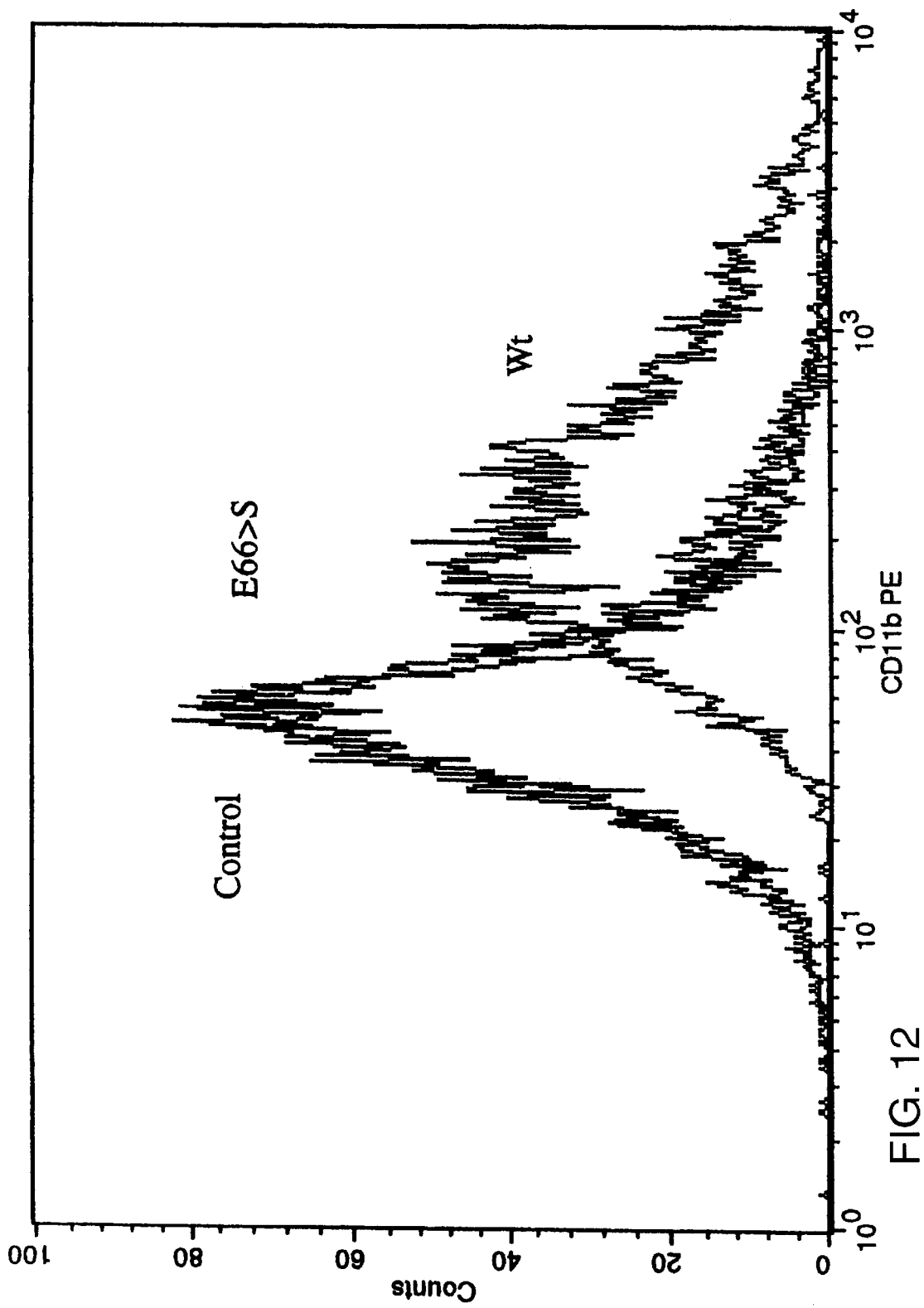

FIG. 12—illustrates the mean fluorescence peak of anti-CD11b monoclonal antibody on wild-type RANTES treated and E66>S disaggregated RANTES treated cells (what type/what concentration). CD11b expression can be seen to be induced on exposure to wild-type RANTES but not by the disaggregated RANTES mutant.

Figure 13:
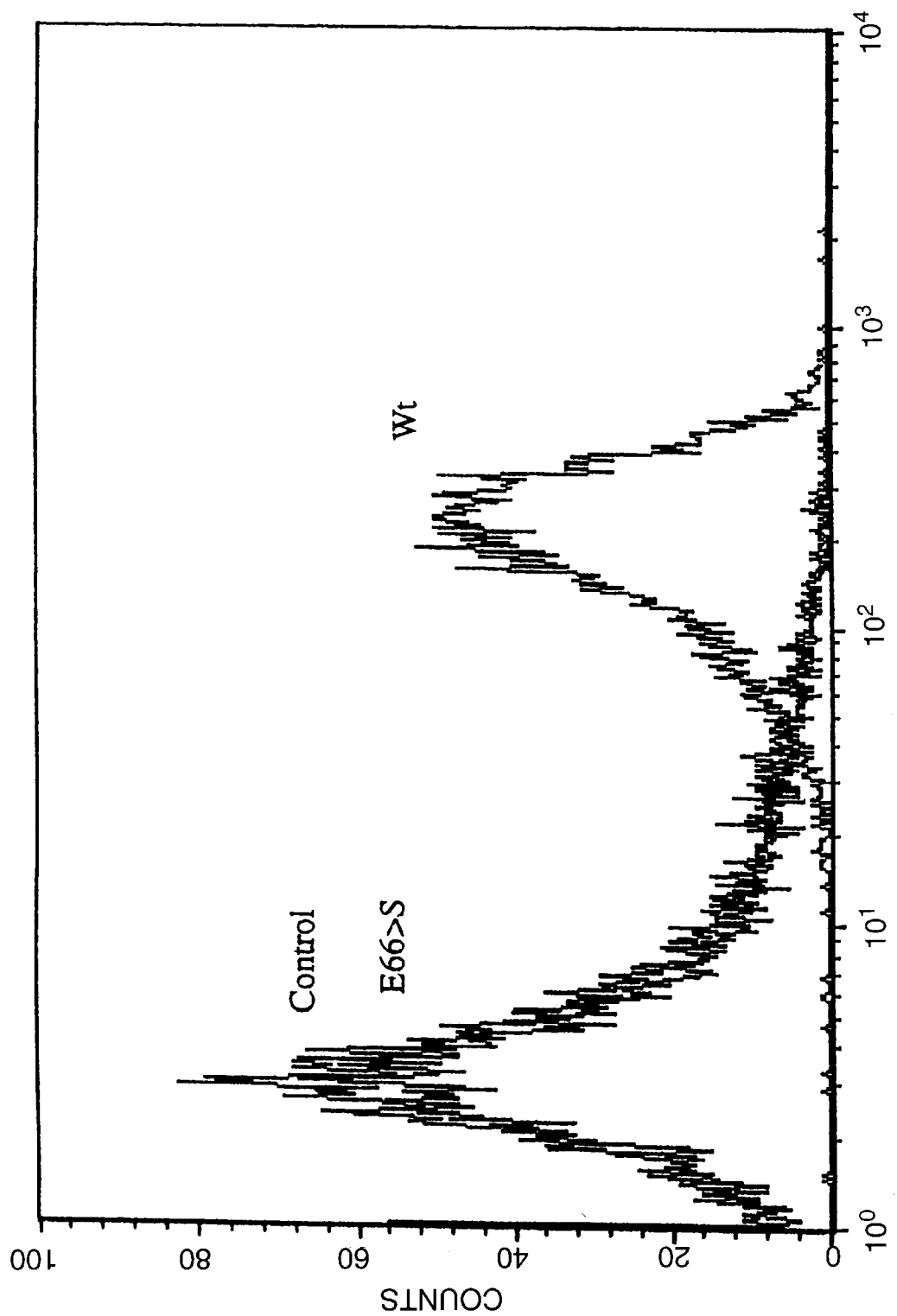

FIG. 13—illustrates the mean fluorescence peak of anti-CD69 monoclonal antibody on wild-type RANTES treated and E66>S disaggregated RANTES treated cells (what type/what concentration). CD69 expression can be seen to be induced on exposure to wild-type RANTES but not by the disaggregated RANTES mutant.

Figure 14:
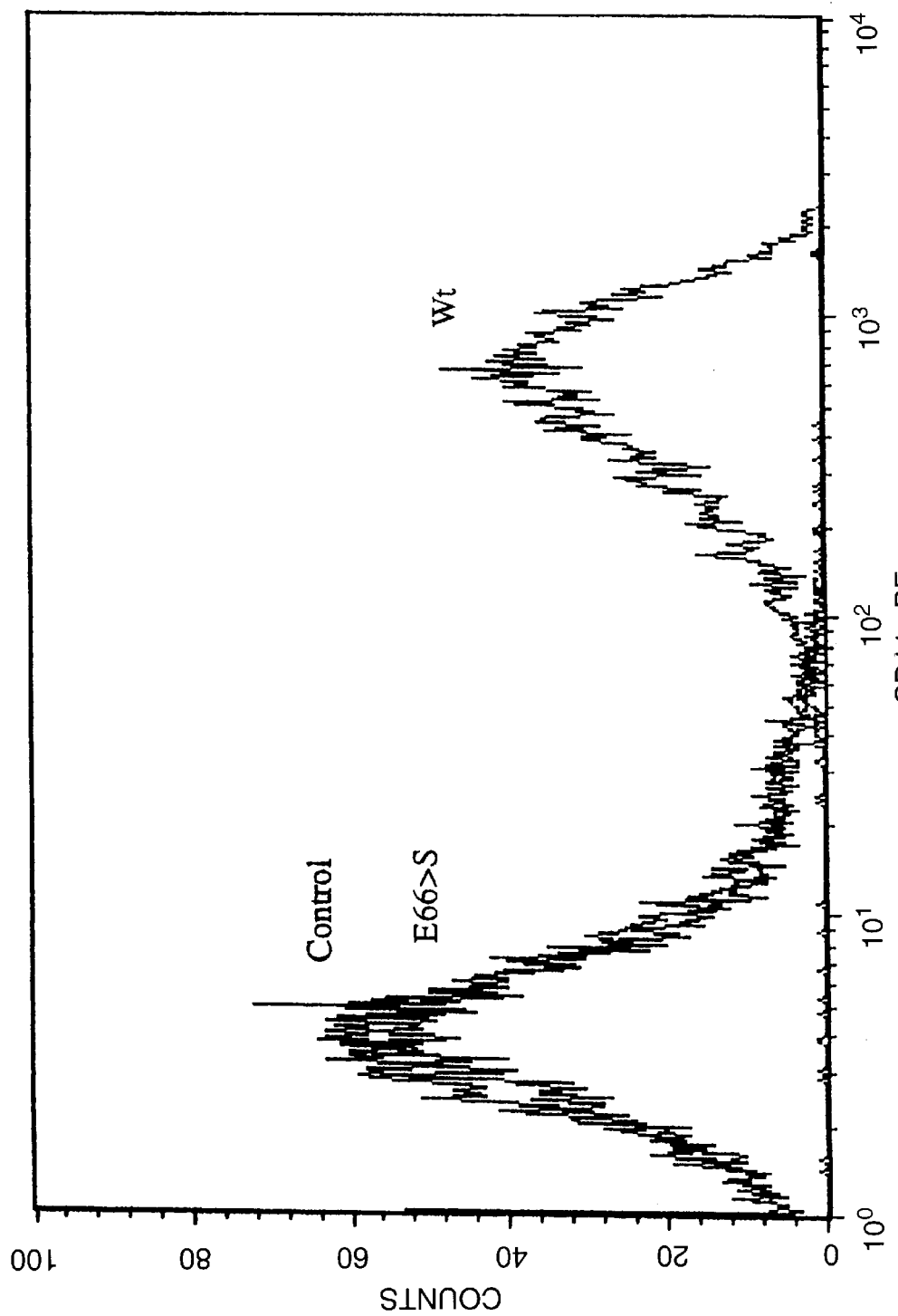

FIG. 14—illustrates the mean fluorescence peak of anti-CD11c monoclonal antibody on wild-type RANTES treated and E66>S disaggregated RANTES treated cells (what type/what concentration). CD1 lc expression can be seen to be induced on exposure to wild-type RANTES but not by the disaggregated RANTES mutant.

Figure 15:
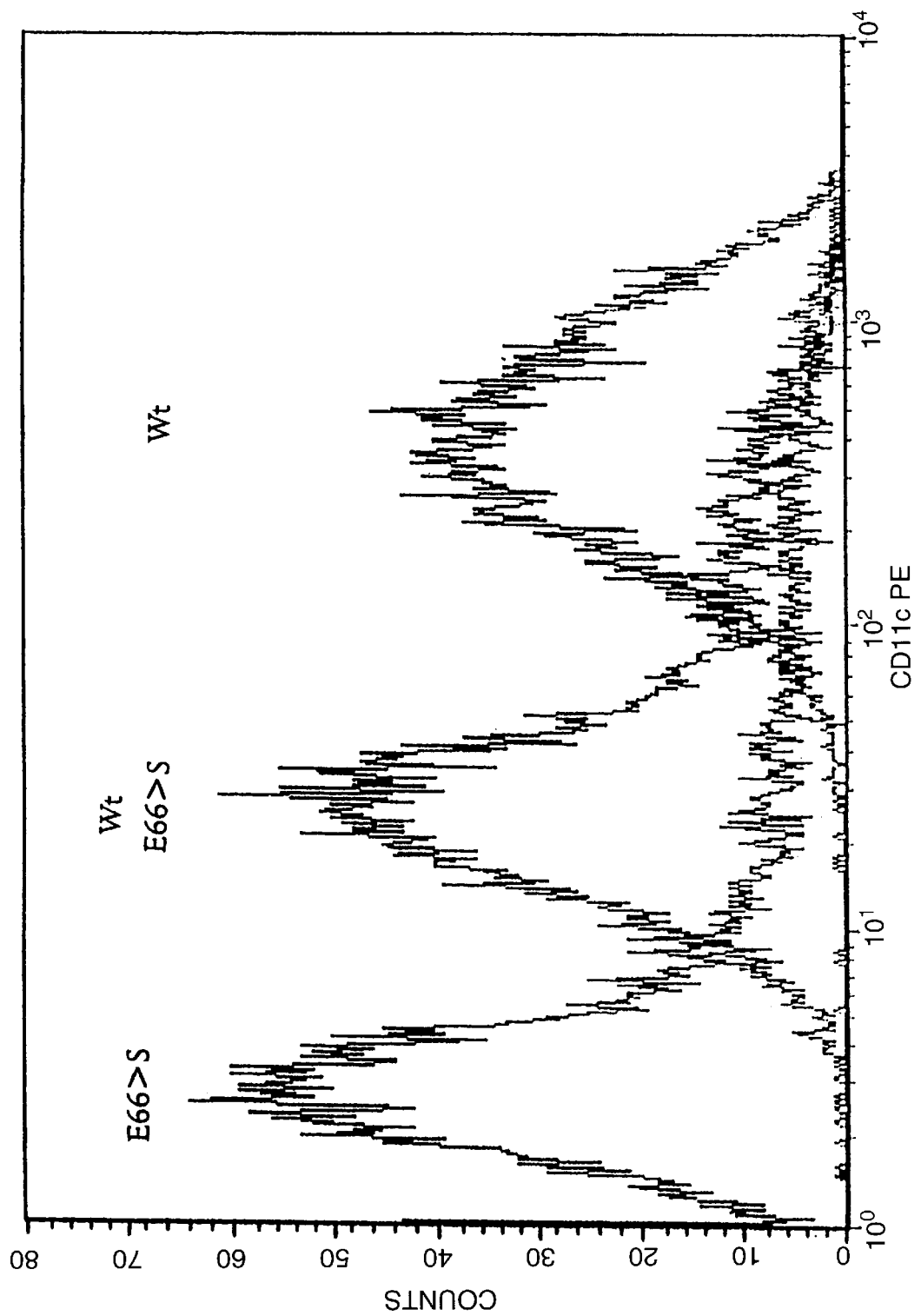

FIG. 15—illustrates the ability of hRANTES E66>S to antagonise the pro-inflammatory activity of hRANTES as determined by CD11c induction. A fourfold excess of hRANTES E66>S substantially inhibits the quantity of CD11c induced by hRANTES.

Figure 16:
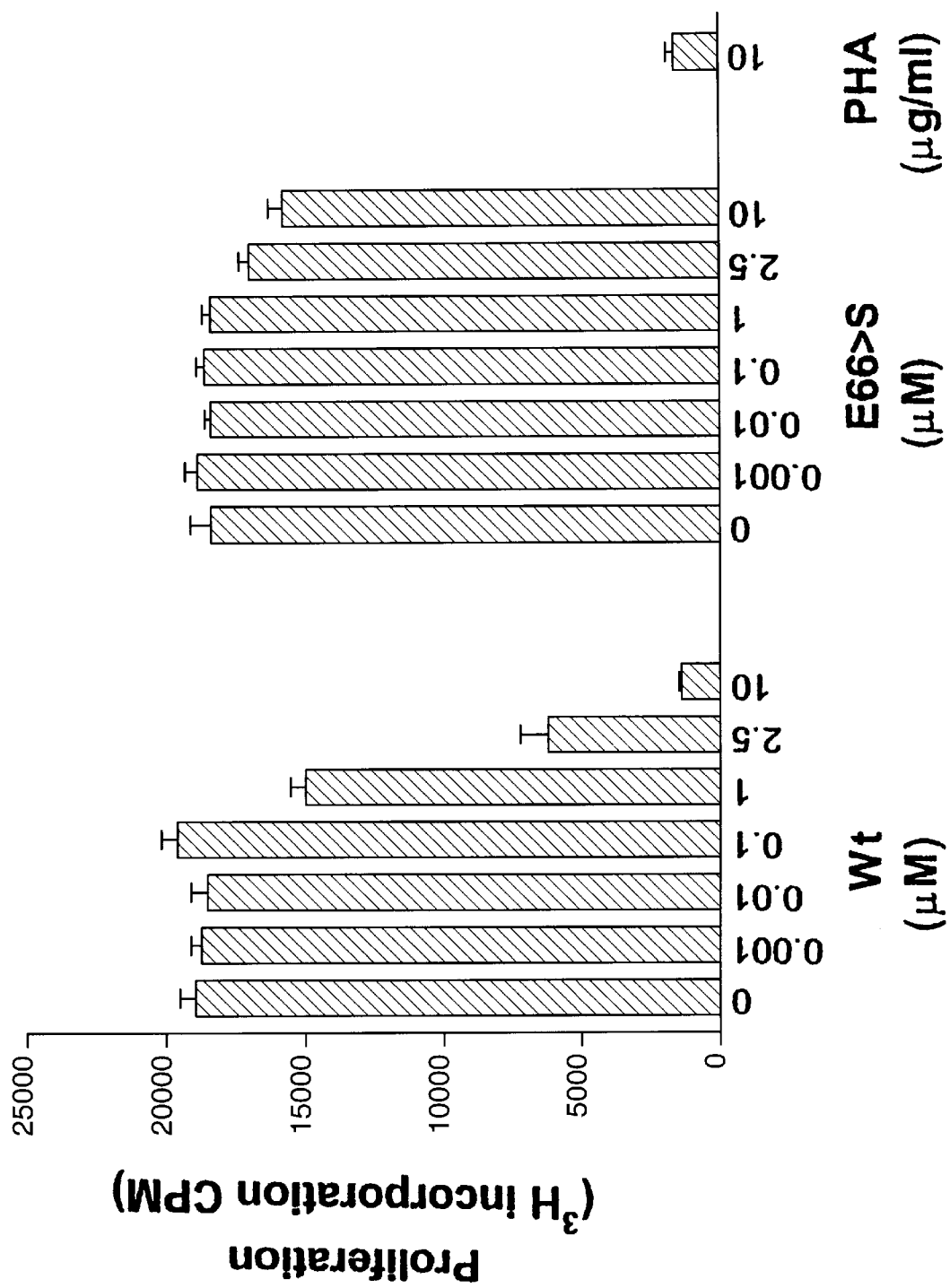

FIG. 16—illustrates the proliferation (measured according to the amount of incorporation of $^3$H thymidine) of Jurkat cells as a function of the wild-type or disaggregated mutant RANTES concentration.

Figure 17:
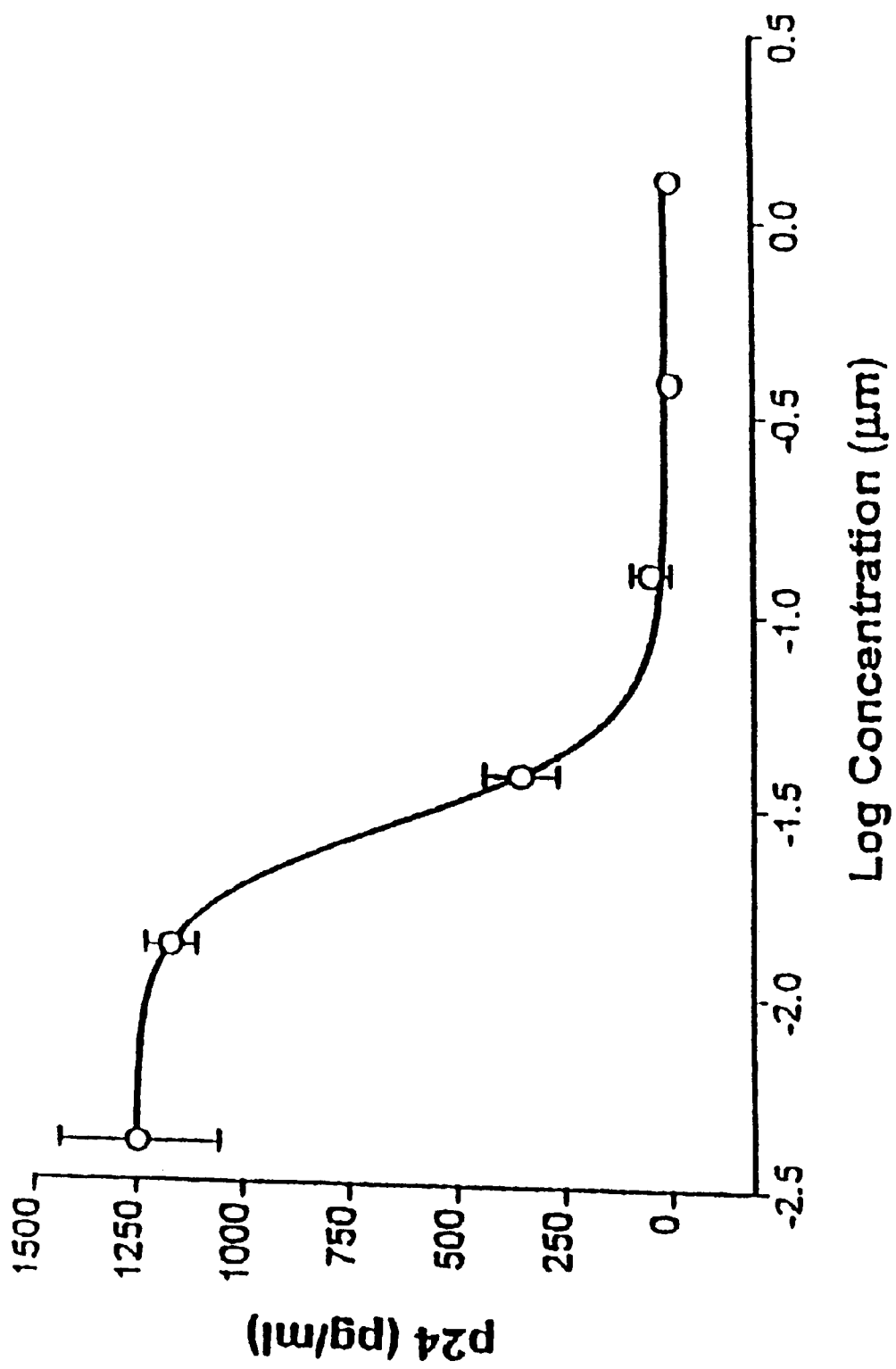

FIG. 17—demonstrates the in vitro suppression of HIV-1 by the E26>A disaggregated RANTES mutant.

EXAMPLES

EXAMPLE 1

Construction of disaggregated hRANTES variants that are substantially incapable at physiological ionic strength of forming a stable multimer higher than a dodecamer.

Many of the techniques of genetic engineering and genetic manipulation used in these examples are detailed in standard laboratory manuals (e.g. Ausubel et al., Current Protocols in Molecular Biology. Volumes 1 and 2. New York: Wiley-lnterscience, 1990., and Sambrook et al., Molecular Cloning, A Laboratory Manual. 2nd ed. New York: Cold Spring Harbor Laboratory Press, 1989). All yeast media were as described by Sherman et al., (Methods in Yeast Genetics, Cold Spring Harbor Laboratory; 1986).

EXAMPLE 1a

Construction of a synthetic hRANTES gene and yeast expression vector

A synthetic gene for hRANTES was designed using the hRANTES protein sequence (SEQ ID No: 1) from the Swissprot data base (Accession Number P13501). The DNA sequence was back-translated and the codon usage was optimised by choosing codons preferred by S. cerevisiae. To enable expression and secretion of the protein from yeast cells, the 5' end of the synthetic gene was designed to include codons for the last five amino acid residues of (Ser Leu Asp Lys Arg) of the yeast mating type factor alpha secretion signal. The sequence was further modified to include a HindIII at the 5' end and a BamHI restriction site at the 3' end. The designed gene was divided into 10 oligonucleotides (SEQ ID NOs: 2–11 respectively): BB-36175 5'-AGCTTGGATA AAAGATCTCC ATATTCTTCA GACACCACAC CTTGCTGT-3'; BB-36039 5'-AAGCAAAACA GCAAGGTGTG GTGTCTGAAG MTATGGAGA TCTTTTATCC A-3'; BB-36040 5'-TTTGCTTACA TTGCTAGGCC TTTGCCTCGT GCCCACATCA AG-3'; BB36041 5'-AATATTCCTT GATGTGGGCA CGAGGCAAAG GCCTAGCAAT GT-3'; BB-35876 5'-GAATATTTCT ACACTTCTGG TAAGTGCTCC AACCCTGCAG TTGTCTTTG-3'; BB-35871 5'-CTGGTCACM AGACMCTGC AGGGTTGGAG CACTTACCAG AAGTGTAGA-3'; BB-36038 5'-TGACCAGAAA GAACCGTCAA GTTTGTGCCA ACCCAGAGAA GAAATGG-3'; BB-35866

5'-CTCTAACCCA TTTCTTCTCT GGGTTGGCAC AAACTTGACG GTTC1T-1-3'; BB-36061 5'-GTTAGAGAAT ACATTMCTC TTTGGAGATG TCCTAATAAG-3'; BB-36176 5'-GATCCTTATT AGGA-CATCTC CAAAGAGTTA ATGTATT-3'. Oligonucleotides were purchased from R+D Systems Europe Ltd., 4–10 The Quadrant, Barton Lane, Abingdon, Oxon OX14 3YS U.K. The oligonucleotides were annealed and cloned into M13mp19 to provide a vector which may be used for subsequent mutagenesis prior to cloning into a yeast expression vector. Recombinant M13mp19 clones containing the hRANTES gene were sequenced with the M13–40 sequencing primer (United States Biochemical Corporation, P.O. Box 22400, Cleveland, Ohio 44122, U.S.A., 5'-GTTTTCCCAGTCACGAC-3') using the dideoxy sequencing method for single-stranded DNA. SEQ ID No: 12 depicts the DNA sequence of the synthetic hRANTES gene including the restriction endonuclease cleavage sites at either end, the stop codons at the 3'end and the 5 amino acid alpha-factor adapter coding sequence at the 5' end. SEQ ID No: 13. depicts the translated amino acid sequences of SEQ ID No: 12. One recombinant clone, pERM1, was chosen since it had an insert with the correct sequence for hRANTES. A vector for the secretion of wild-type hRANTES from *S. cerevisiae*, pERS1, was created by transferring the hRANTES gene from pERM1 as a ca. 230bp. HindIII and BamHI DNA fragment into the yeast expression vector pSW6 (Clements et al., Cytokine. 4:76, 1992). The vector contains an expression cassette in which the synthetic hRANTES gene is under the control of a galactose-inducible promoter. The specific use of plasmid pSW6 in this example is not essential to the working of the invention. The person skilled in the art would appreciate that numerous suitable alternative plasmids could used.

EXAMPLE 1b

Construction of variant hRANTES genes

Mutagenesis of pERM1 was performed according to the method of Kunkel et al., (Methods in Enzymology, 154: 367–382; 1987). The oligonucleotides BB-35875 (SEQ ID NO. 14; 5'-GTGTAGAAAT AAGCCTTGAT GTGG-3') and BB-37015 (SEQ ID No. 15; 5'-CCTTATTAGG ACATTGA-CAA GGAGTTAATG-3') were used to construct the hRANTES Glu26>Ala and Glu66>Ser variant genes respectively. A combination of both BB-35875 and BB-37015 was used to construct a mutant gene containing both the Glu26>Ala and Glu66>Ser substitutions. Dideoxy sequencing (Sequenase 2.0, United States Biochemical Corporation, P.O. Box 22400, Cleveland, Ohio 44122, U.S.A.) was used to identify a correct clone for each variant. Each variant gene was then sub-cloned into the yeast expression vector pSW6 using HindIII and BamHI. The recombinant pSW6 clones containing the mutated hRANTES genes were sequenced using the dideoxy sequencing method for double stranded DNA.

Glu26>Ala (or E26>A) refers to the substitution at amino acid position 26 of the wild-type glutamic acid by alanine. Glu66>Ser (or E66>S) refers to the substitution at amino acid position 66 of the wild-type glutamic acid by serine. Glu26>Ala and Glu66>Ser (or E26>A+E66>S) refers to the double substitution at amino acid position 26 and 66 of the wild-type glutamic acids with alanine and serine respectively. The nomenclature for the expression vectors is described in the table in Example 1*e*.

EXAMPLE 1*c*

Production of hRANTES proteins from *S. cerevisiae*

S. cerevisiaestrain MC2 (genotype: prg-1–407, prg-1–122, pep4–3, leu23–112, trp1, ura3–52 mating type a) was transformed with DNA containing the wild-type and mutant hRANTES genes by the LiAc/PEG protocol (Gietz et al., Nucl. Acid Res. 20:1425, 1992) and then plated onto SC-glu-agar plates and allowed to grow for 4–5 days at 30° C. After 4–5 days, transformants were picked and streaked onto fresh SC-glu-agar plates to provide single colonies. These were used to inoculate 5 ml of SC-glu-broth for overnight seed cultures which were used to inoculate 100 ml of Sc-glu broth in 0.5 L flasks. After 24 hrs growth at 30° C., the cells were used to inoculate the SC-glu/gal-expression culture-broth (100 ml) in a 2L baffled-flask and was grown in a shaking incubator at 30° C. for 3 days.

The use of strain MC2 is not critical for use either in this preparation or in the invention in general. Any suitable strain which is genetically similar to MC2 can be used.

EXAMPLE 1*d*

Harvesting and purification of hRANTES protein

After three days of expression, HPLC was used to identify the best expressing clone of each variant for harvest. A sample of the culture (1 ml) was removed from the culture for DNA recovery to verify the identity of the substitution by DNA sequencing. The cell-free supernatant from the rest of the culture was either used immediately for protein purification, or it was filter sterilised (0.2 $\mu$M Nalgene cellulose acetate filtration unit) and stored at 4° C. for short periods (1–2 days) or −20° C. for longer periods.

The hRANTES proteins were purified from the yeast culture supernatants according to the methods described by Patel et al., (Biochemistry. 32: 5466;1993). Both ion-exchange and reverse-phase HPLC chromatography were used to isolate the protein to >95% purity. Briefly, cell-free supernatant was adjusted to pH8 and batch-adsorbed onto pre-equilibrated (50 mM HEPES, pH8.0) Q-sepharose (Pharmacia). Protein was eluted from the resin in 50 mM HEPES, 1 M NaCl, pH8.0 and dialysed in a 3 KDa cutoff membrane against 10 volumes of 5 mM Tris, pH8.0, at 4° C. The sample was then loaded onto a 20 ml VYDAC C-18 (10 $\mu$M) pre-equilibrated semi-preparative reverse-phase column at 5 ml/min. hRANTES and variants were eluted at >95% purity with a linear gradient from 20% to 60% (v/v) acetonitrile/0.1% trifluoroacetic acid over 40 mins. Eluting fractions were detected by UV absorbance at 280 nM, they were pooled and the purified protein lyophilised. The amino acid sequence of the purified proteins are shown in SEQ ID No: 1 (hRANTES), SEQ ID No: 16 (hRANTES E26>A), SEQ ID No: 17 (hRANTES E66>S) and SEQ ID No: 18 (hRANTES E26>A E66>S).

EXAMPLE 1*e*

Assessing the multimerisation state by sedimentation equilibrium AUC.

Sedimentation equilibrium AUC was performed using a Beckman XLA analytical ultracentrifuge with absorbance optics as described by Patel et al., (Biochemistry 32: 5466; 1993). Protein samples at 0.5 mg/ml were loaded in a six sector cell to enable simultaneous measurements and comparisons of variants. Wild-type hRANTES aggregated so readily that at 0.5 mg/ml reliable data could not be collected. Wild-type hRANTES was therefore analysed at 0.1 mg/ml to allow collection of data. PBS "A" was loaded in the reference sector. The samples were spun at 15,000 r.p.m., 25° C. for 18 hours to reach equilibrium. Final solute distributions were recorded at 235 nm, 280 nm and 295 nm as a function of radius. The scan was repeated after a further three hours of centrifugation to confirm that equilibrium had been achieved. The final solute distribution ASCII data were captured and the Microcal Origin software for the Beckman XLA analytical ultracentrifuge was used to fit the data to a model assuming a single ideal species (Ideal1) to provide an estimate of the weight average molecular weight.

AUC analysis of the three disaggregated forms of hRANTES show that they have a much reduced tendency to aggregate and are substantially incapable of forming stable multimers higher than dodecamers as determined by AUC at 0.5 mg/ml (0.1 mg/ml for wild type RANTES) in physiological conditions (FIGS. 1 to 4). The approximate average molecular weights of the three mutant hRANTES proteins are shown in table 1 below.

TABLE 1

| Corresponding Yeast Expression Vector | Variant Carried | Average molecular weight by AUC (Da) |
| --- | --- | --- |
| pERS1 | Wild Type hRANTES | >160,000 (0.1 mg/ml) |
| pERS2 | hRANTES Glu26>Ala | 33,000 (0.5 mg/ml) |
| pERS3 | hRANTES Glu66>Ser | 14,000 (0.5 mg/ml) |
| pERS4 | hRANTES Glu26>Ala, Glu66>Ser | 15,000 (0.5 mg/ml) |

These results demonstrate that wild-type hRANTES is an aggregating chemokine which at 0.1 mg/ml has an average molecular weight in excess of 160,000 Da. This is in excess of a dodecamer of its monomeric units, each of which has a mass of 7850Da. At 0.5 mg/ml the aggregation was too great to allow collection of reliable data. Since the aggregation phenomenon of chemokines is concentration dependent, those skilled in the art would appreciate that the 0.1 mg/ml result would be an underestimate of the average molecular weight at 0.5 mg/ml.

The disaggregated hRANTES mutants all have average molecular weights at 0.5 mg/ml which are less than 94,200Da (the size of a dodecamer of hRANTES). The E26>A substitution appears to inhibit the formation of multimers greater than tetramers while the E66>S substitution blocks the formation of multimers greater than dimers of hRANTES.

EXAMPLE 2

Assessing the biological activity of the disaggregated RANTES mutants on the GPCR pathway.

Bacon et al. (1995, ibid) describes suitable assays to determine whether the GPCR pathway and/or the T-cell receptor mediated signal transduction pathway is activated by hRANTES. The inventors have chosen the calcium mobilisation assay used by Bacon et al. as their preferred assay to estimate the pro-inflammatory/lymphocyte activating properties of the hRANTES variants. The two hRANTES signalling pathways can be studied independently by use of THP-1 and CD3+ Jurkat cell lines which have the GPCR and TK signal transduction pathways respectively. The use of cell lines allows greater reproducibility over time and easier tissue preparation. In this example, THP-1 cells were used in order to demonstrate that the disaggregated hRANTES variants are able to transduce a signal at GPCRs, ie. that they are potent agonists. In the next example CD3+Jurkat cells were used to investigate whether disaggregated hRANTES activated the T-cell receptor complex tyrosine kinase pathway.

EXAMPLE 2a

Calcium mobilisation by hRANTES and disaggregated hRANTES mutants in THP-1 cells (monocytes). The activities of hRANTES and the disaggregated hRANTES mutants were assessed at 50 nM and 1 $\mu$M concentrations in a standard calcium mobilisation assay using THP-1 cells. The THP-1 cells lack the tyrosine kinase pathway, but respond to hRANTES via the GPCR mediated signal transduction pathway. Their use allows confirmation of the biological activity of the proteins on this pathway. This assay is described in Hunter et al., Blood 86:4400–4408, 1995) and is described briefly below.

The human monocytic cell-line THP-1 (ECACC No: 88081201) was cultured in RPMI 1640 medium containing 2 mM glutamine, 10% (v/v) fetal calf serum. The cells were maintained at a density of between 1 and $8 \times 10^5$ cells/ml, incubated at 37° C., in an atmosphere of 95% air/5% $CO_2$. Changes in the concentration of intracellular $Ca^{2+}$ were followed using the fluorescent label FURA-2 (Sozzani et al., J. Immunol 150: 1544, 1993. THP-1 cells were harvested and resuspended to $2-3 \times 10^6$ cells/ml in growth medium. FURA-2AM (Cambridge Bioscience, 1 mg/ml in DMSO) was added to 1 $\mu$M and incubated for 45 min at 37° C., in an atmosphere of 95% air/5% $CO_2$. The cells were washed and resuspended in Tyrodes buffer (10 mM HEPES, 129 mM NaCl, 8.9 mM $NaHCO_3$, 2.8 mM KCl, 0.8 mM $KH_2PO_4$, 5.6mM dextrose, 0.8 mM $MgCl_2$ pH7.4) to give $23 \times 10^6$ THP-1 cells/ml. FURA-2 fluorescence emission intensity was measured at 37° C. using a Perkin-Elmer LS-50 fluorimeter with a cell holder and built in magnetic stirrer. The samples were excited at 340 nm with a 10 nm bandwidth and the emission continuously recorded at 500 nm with a 5 nm bandwidth. FURA-2 loaded THP-1 cells (2 ml, $2 \times 10^6$ cells/ml) were transferred to a 4.5 ml UV grade PMMA cuvette (Kartell disposable UV grade PMMA cuvette, Fisons); $CaCl_2$ was added to 1 mM and left to equilibrate for 2 min. hRANTES or disaggregated mutants were added (20 $\mu$l 100x final concentration) and the increase in intracellular calcium noted. To obtain maximum fluorescence in 1 mM $Ca^{2+}$ ($F_{max}$) digitonin (20 $\mu$l 5 mM digitonin (Sigma) in ethanol; a saturated solution) was added to lyse the cells. Once the fluorescence level had stabilised, EGTA (20 $\mu$l 1 M EGTA (BDH) pH7.2) was added to obtain the background fluorescence ($F_{min}$). The increase in intracellular calcium was calculated according to the equation $[Ca^{2+}]i$ nM=224 $[(F2-F_{min})/(F_{max}-F2)]-224 [(F1-F_{min})/(F_{max}-F1)]$, where F1=intensity prior to agonist addition, F2=peak intensity after agonist addition, $F_{max}$=intensity after digitonin addition, Fmin=intensity after EGTA chelation.

Figure 1:
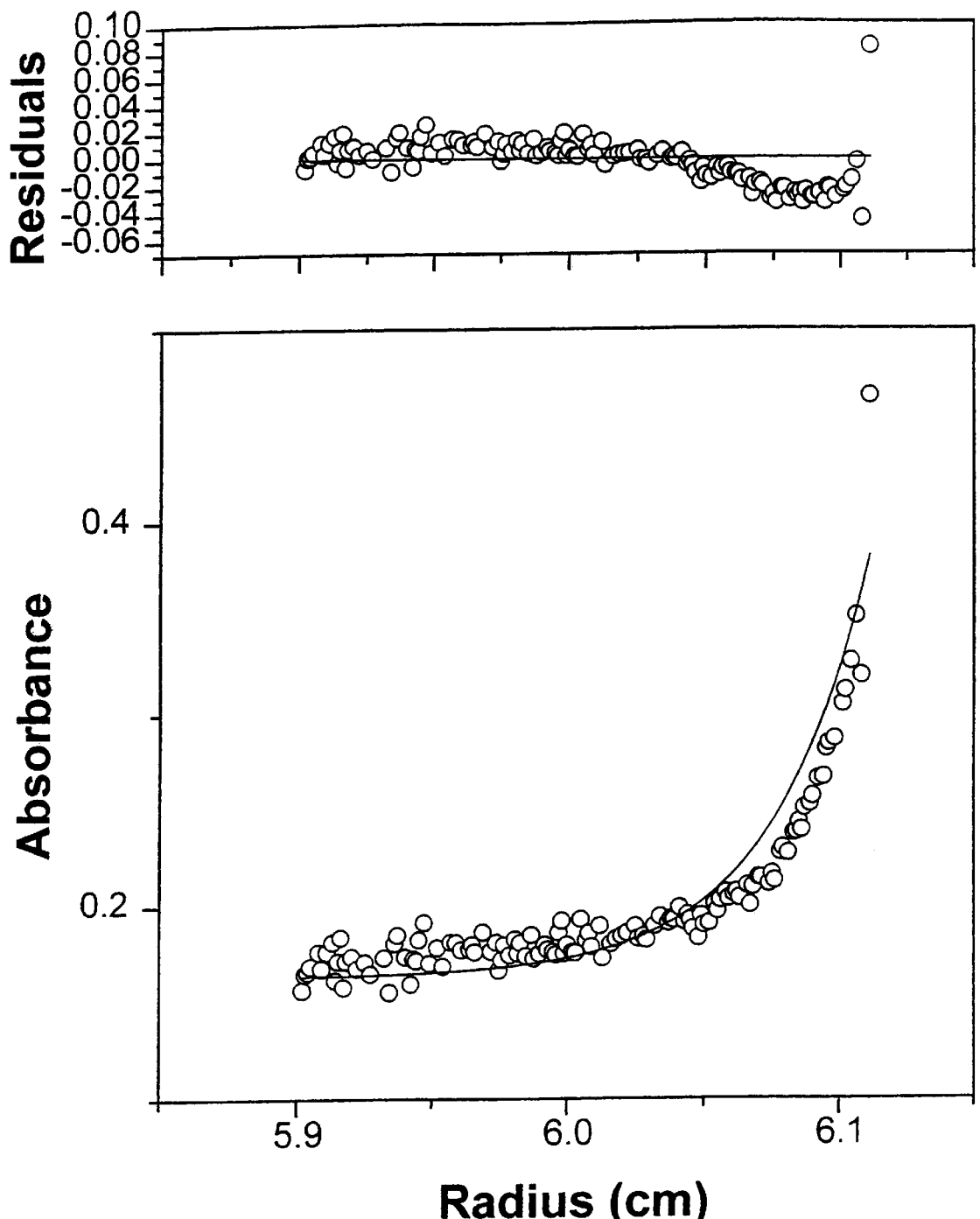
FIG. 1—illustrates the aggregation properties of wild-type hRANTES at 0.1 mg/ml in PBS as determined by analytical ultracentrifugation.
Figure 2:
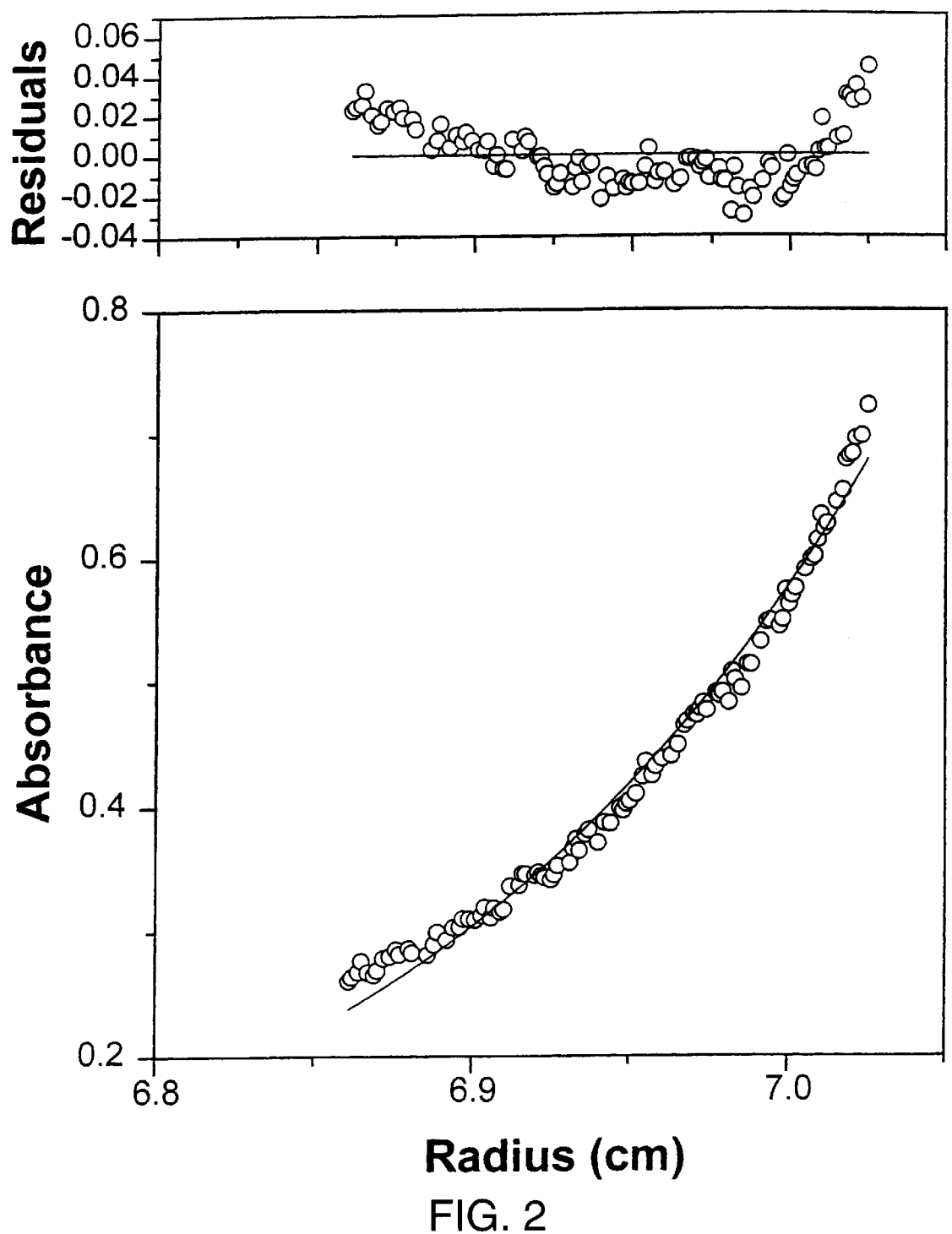
FIG. 2—illustrates the aggregation properties of hRANTES E26>A at 0.5 mg/ml in PBS as determined by analytical ultracentrifugation.
Figure 3:
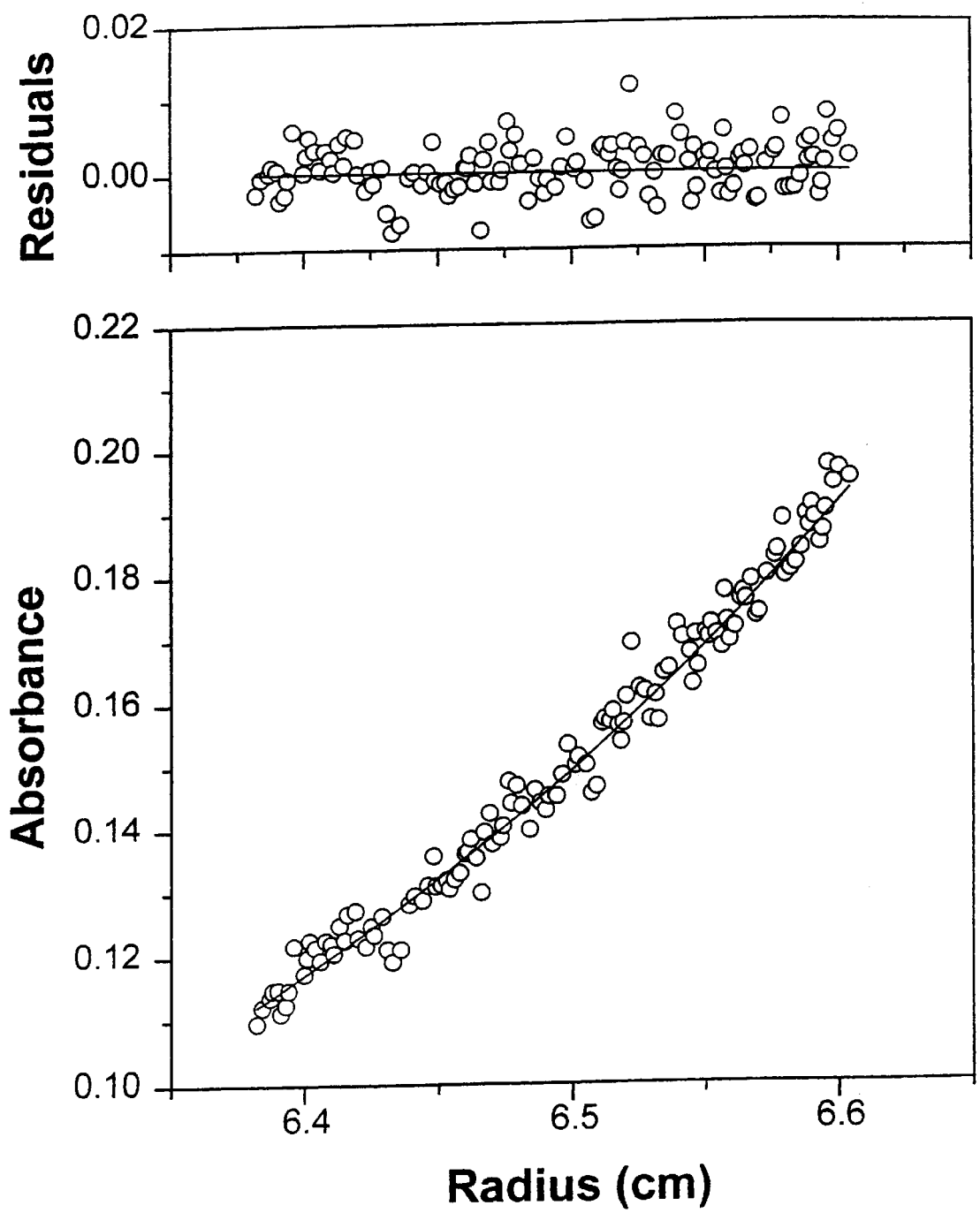
FIG. 3—illustrates the aggregation properties of hRANTES E66>S at 0.5 mg/ml in PBS as determined by analytical ultracentrifugation.
Figure 4:
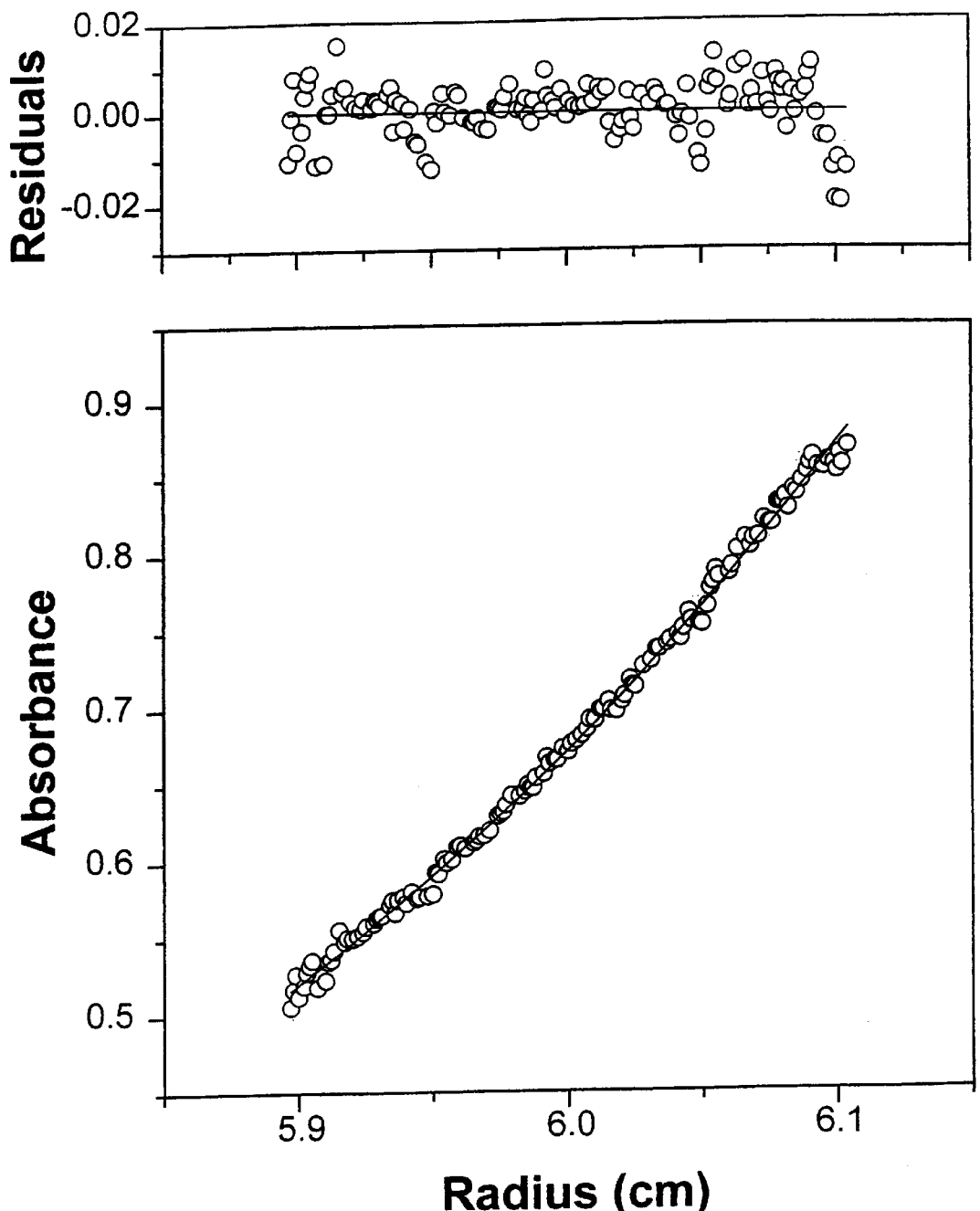
FIG. 4—illustrates the aggregation properties of hRANTES E26>A E66>S at 0.5 mg/ml in PBS as determined by analytical ultracentrifugation.
Figure 5:
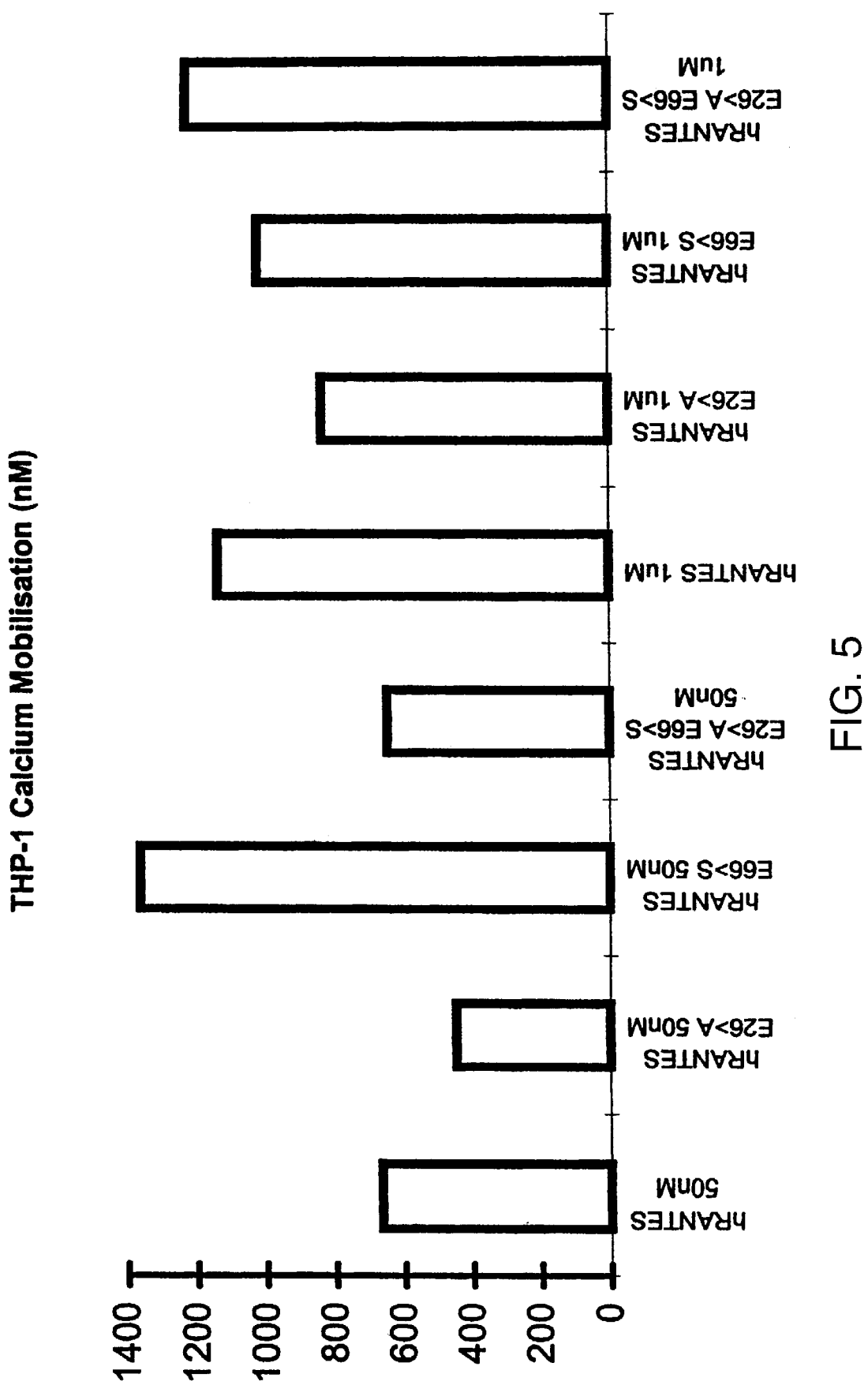
FIG. 5—illustrates the calcium mobilisation (nM) in THP-1 cells by hRANTES and disaggregated hRANTES variants at 50 nM and 1 μM.
Figure 6:
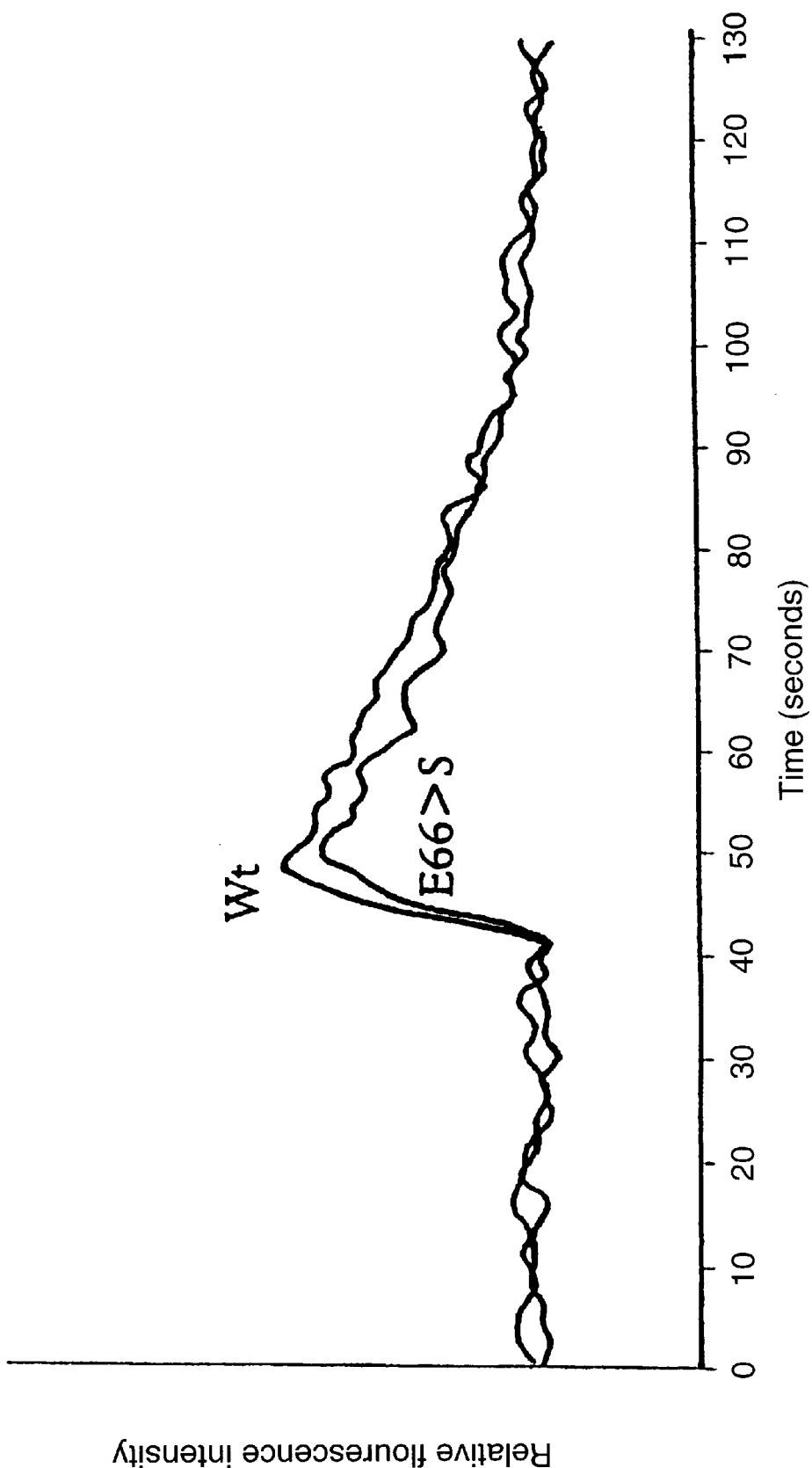
FIG. 6—illustrates the typical transient calcium mobilisation response on THP-1 cells induced by 1 μM wild-type RANTES and E66>S disaggregated RANTES mutant. Equivalent responses can be seen.
Figure 7:
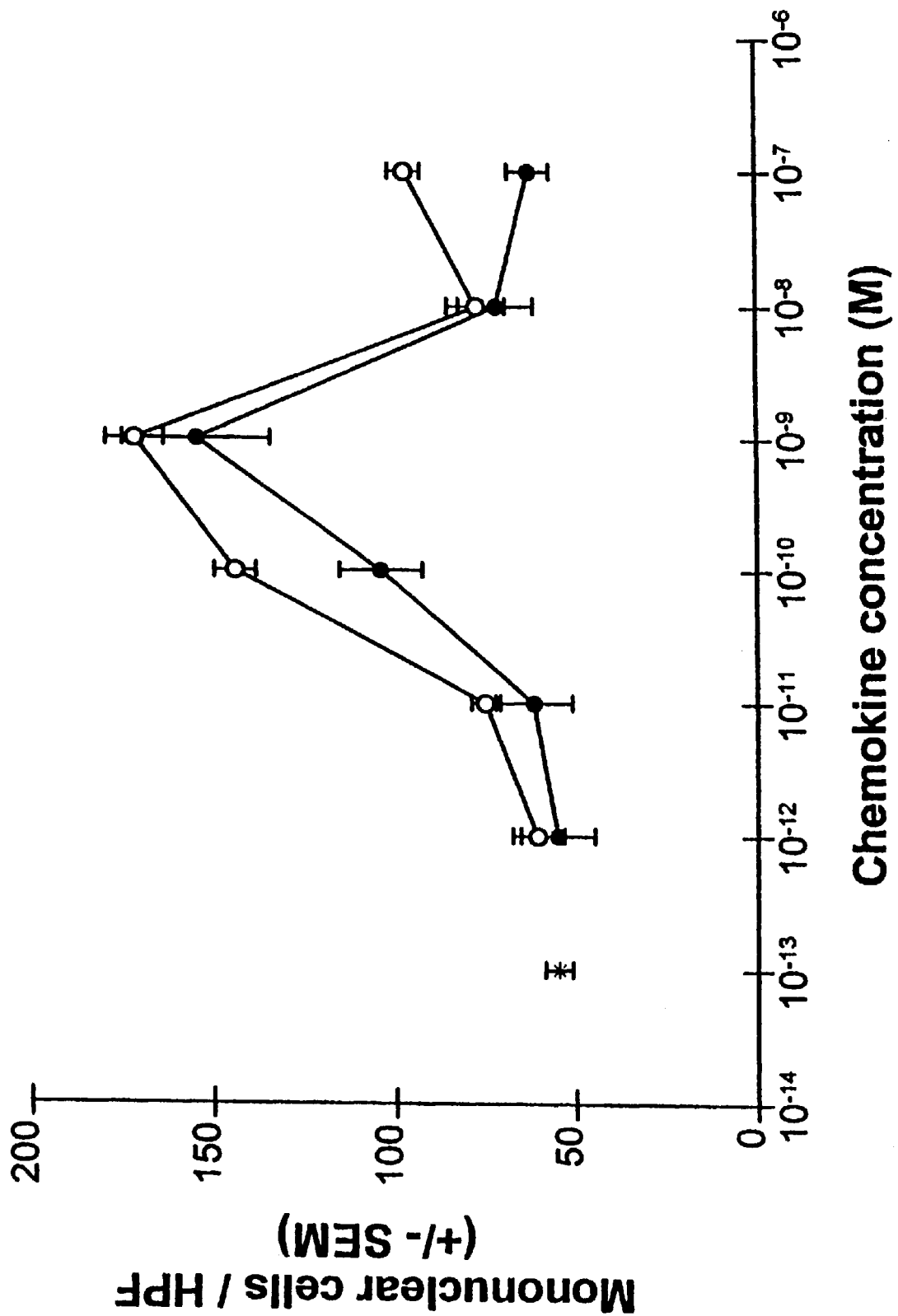
FIG. 7—illustrates the degree of chemotaxis of mononuclear cells in response to different concentrations of wild-type or E66>S disaggregated mutant RANTES.
Figure 8:
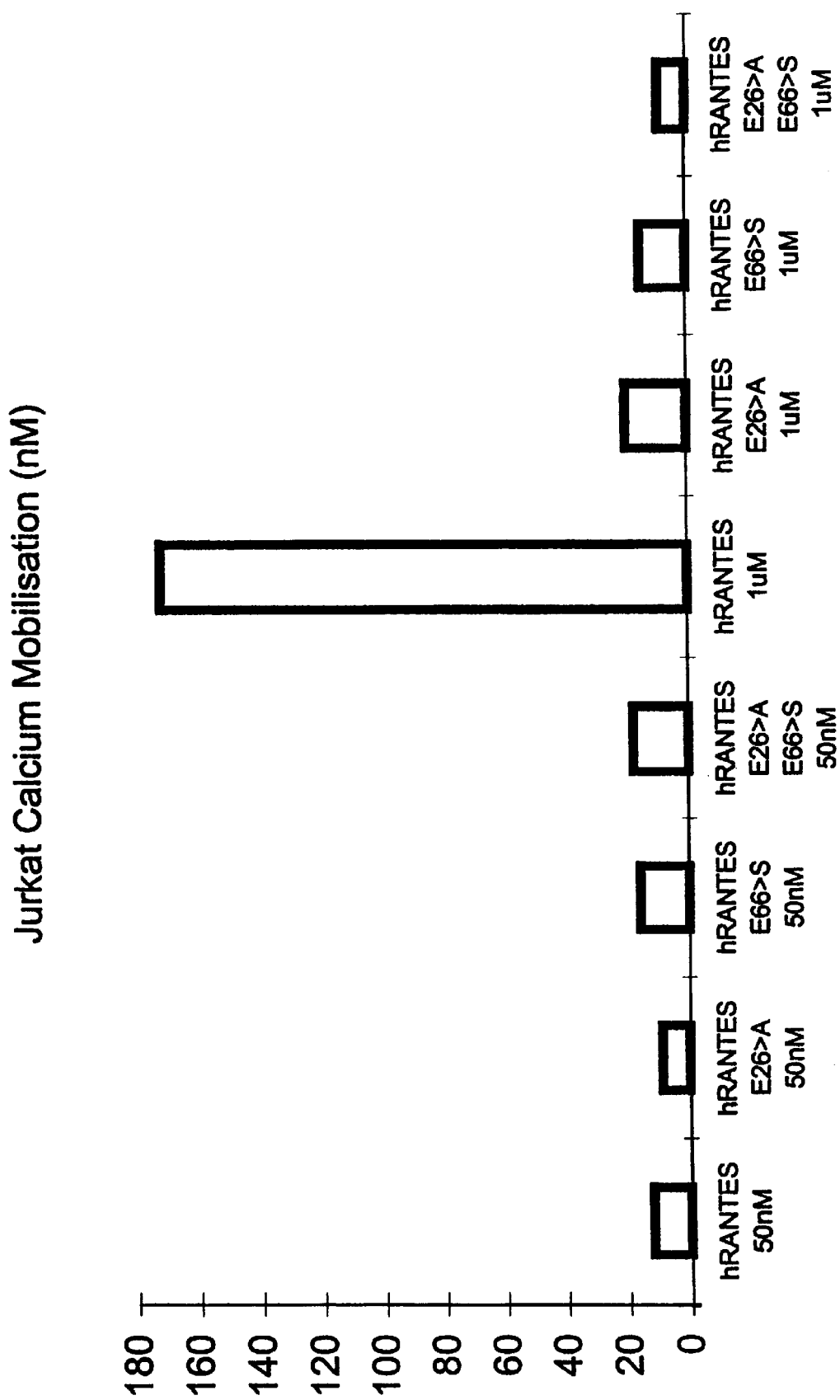
FIG. 8—illustrates the calcium mobilisation (nM) in CD3+ Jurkat cells by hRANTES and disaggregated hRANTES variants at 50 nM and 1 μM. Calcium mobilisation is induced by 1 μM wild-type RANTES but not by 1 μM of any of the disaggregated RANTES mutants.
Figure 9:
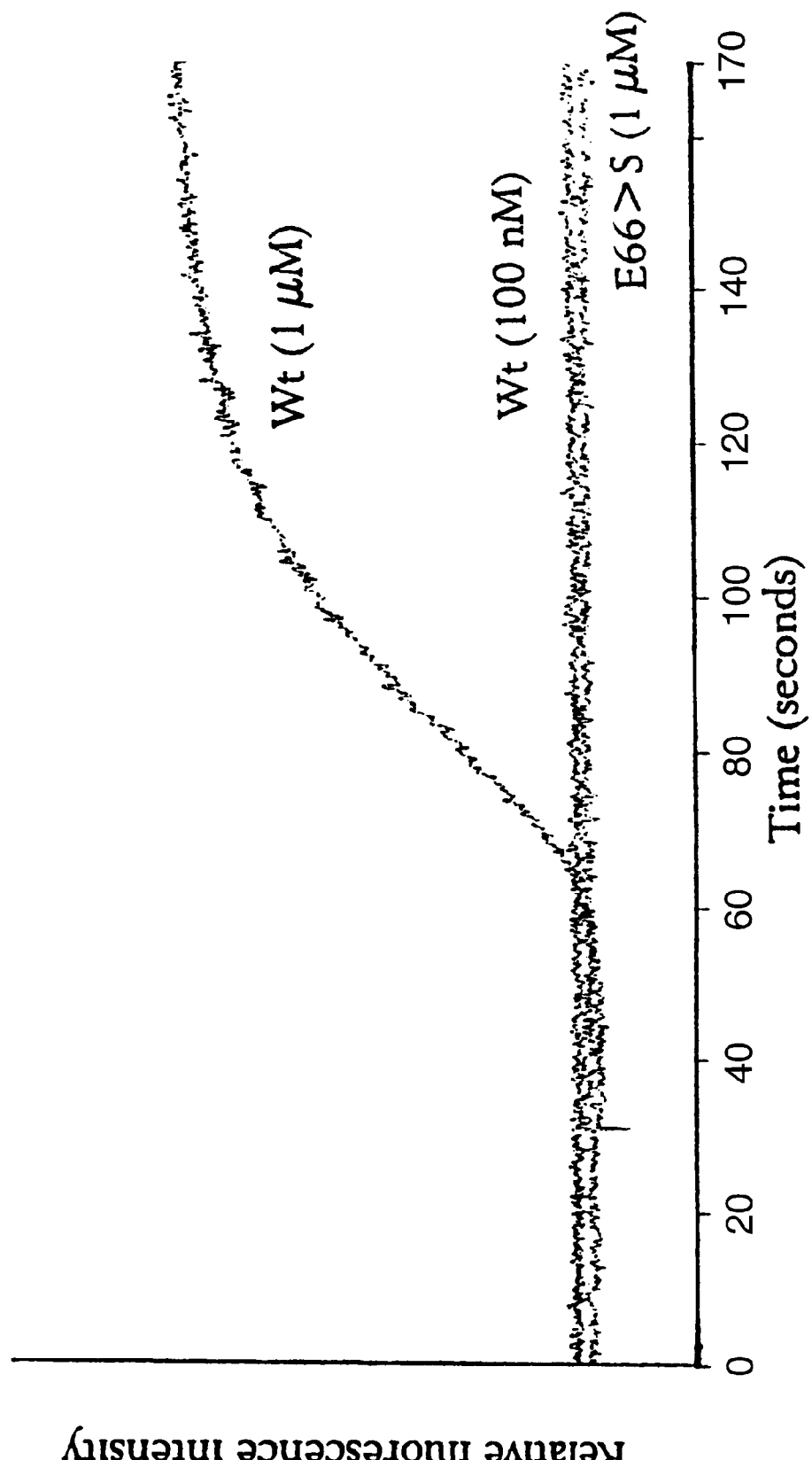
FIG. 9—Illustrates the calcium mobilisation response on Jurkat cells following administration of 100 nM or 1 μM wild-type RANTES, and 1 μM E66>S disaggregated RANTES mutant.
Figure 10:
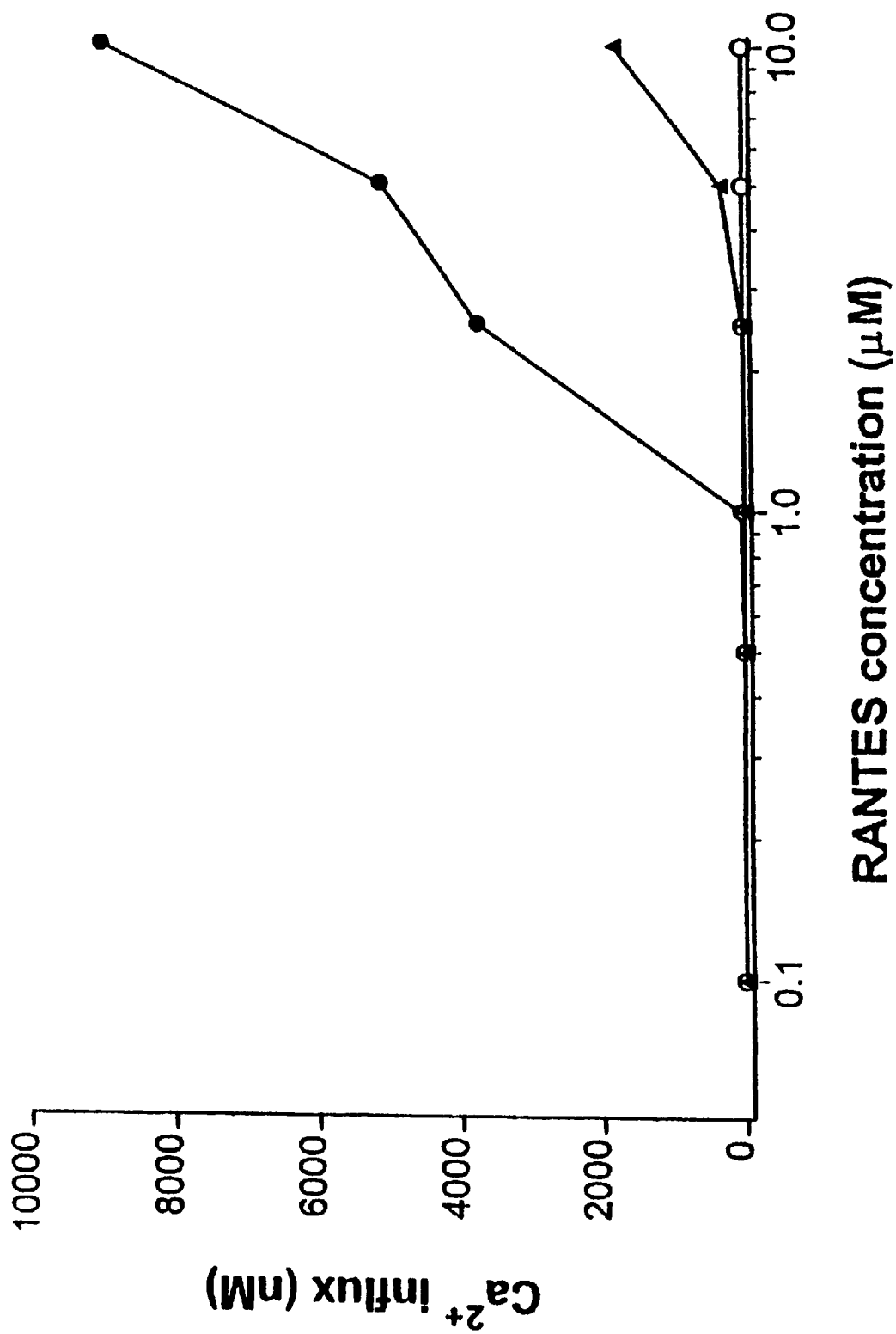
FIG. 10—illustrates a dose response curve of the calcium mobilisation/influx (nM) by wild-type and the disaggregated RANTES mutants on Jurkat cells.

The results of this assay confirm that hRANTES and disaggregated mutants are active agonists which cause a transient calcium mobilisation in THP-1 cells at 50nM and 1 $\mu$M concentrations (FIG. 5). There was little difference in the response to 50 nM and 1 $\mu$M agonist. The mobilisation response was a typical GPCR response of a rapid transient mobilisation of calcium which had reverted to baseline within 120 sec of agonist addition (FIG. 6).

EXAMPLE 2b

Chemotaxis of mononuclear cells by hRANTES and disaggregated hRANTES mutants.

Bacon et al. (ibid) described the link between chemotaxis and activation of the GPCR pathway. Accordingly, chemotaxis assays were performed in order to verify the previously observed biological activity (GPCR activation) seen with the disaggregated RANTES mutants.

Cell migration in response to a gradient of wild-type or E66>S hRANTES mutant were measured using 24-well culture plates containing polycarbonate membrane inserts with 8 μm pore size (Falcon). Freshly purified peripheral blood mononuclear cells (PBMCs) were obtained from normal volunteer donors by venepuncture and cell purification. Blood was centrifuged on Ficoll-Hypaque (Sigma) to remove erythrocytes, granulocytes and cellular debris and mononuclear cells (monocytes and lymphocytes) which banded were collected and washed extensively in PBS. The RANTES proteins were diluted from $10^{-12}$ M to $10^{-7}$ M in fetal calf serum (FCS) free RPMI 1640 medium and 500 μl of each dilution was placed into a separate well. Fresh purified peripheral blood mononuclear cells (monocytes and lymphocytes) were suspended at $2.5\times10^6$ cells/ml in FCS free RPMI-1640 and 200, μl of this suspension was placed onto the insert filters prior to placing the filters into the well. The plates were incubated at 37° C. for 2 hours, the filters removed, dried with tissue and then placed in 4% formaldehyde for 10 minutes to fix the cells. The filters were then washed in PBS, placed in cresyl violet for 10 minutes, and washed again. Cell migration was assessed by counting the number of cells in two high power field (HPR) per well. The data is expressed as the number of counted cells per field. The results are shown in FIG. 7. hRANTES E66>S demonstrates equivalent mononuclear cell chemotaxis as wild-type RANTES, with a maximal migration occurring at approximately $10^{-9}$ M.

EXAMPLE 3

Assessing the biological activity of the disaggregated RANTES mutants on the tyrosine kinase pathway.

The effect of hRANTES and the disaggregated mutants on the T-cell CD3+ Jurkat cell line was assessed using the calcium mobilisation assay described in Example 2*a,* with the exceptions that (1) the THP-1 cells were replaced with Jurkat cells and (2) 1 ml of cells ($4\times10^6$ cells/ml) were added to the cuvette and the test chemokine was added to the cells in the cuvette as a 1 ml solution (2× final concentration). CD3+ Jurkat cells were obtained from the European Collection of Cell Cultures (ECACC; catalogue number 88042803). The CD3+ Jurkat cell-line was cultured in RPMI 1640 medium containing 2 mM glutamine and 10% (vol/vol) fetal calf serum (FCS) at 37° C. in an atmosphere of 95% air/5% $CO_2$. Cells were passaged every 24 days using a split ratio of 1:5.

The CD3+ Jurkat cell line is an immortalised T cell line that does not possess the GPCR mediated signal transduction pathway and can only respond to high concentrations of hRANTES via the T-cell receptor tyrosine kinase mediated pathway. The results are depicted in FIGS. 8 and 9. In agreement with Bacon et al., hRANTES does not cause calcium mobilisation at low concentration (50 nM or 100 nM) but did cause mobilisation at 1 μM. This mobilisation was prolonged, not returning to baseline for several minutes. This confirms that hRANTES is an active agonist on Jurkat cells at high concentration. Surprisingly, the disaggregated hRANTES mutants did not induce calcium mobilisation at either 50 nM, 100 nM or 1 μM concentrations. This demonstrates that the disaggregated hRANTES mutants are not able to elicit the pro-inflammatory/lymphocyte activating response associated with activation via the T-cell receptor. Activation of the TK dependent signal transduction pathway appears to require an aggregating form of hRANTES.

A dose response curve of the calcium mobilisation (from 0.1 μM and 10 μM) of wild-type and disaggregated mutant RANTES on Jurkat cells was performed. The results can be seen in FIG. 10.

Calcium was mobilised by wild-type RANTES at concentrations above 1 μM. The RANTES mutant E26>A (which essentially forms tetramers), began to mobilise calcium when administered at approximately 5 μM. The disaggregated RANTES mutants E66>S and E26>A+E66>S (both of which essentially form dimers) however, did not demonstrate any detectable calcium mobilisation, even when administered at 10 μM.

In order to look at the effects of disaggregated mutant RANTES at concentrations that would be appropriate for an injectable therapeutic formulation, the calcium mobilisation assay was performed on Jurkat cells with very high concentrations of the RANTES mutant E66>S. When administered at 500 μM, the disaggregated RANTES mutant E66>S was capable of mobilising calcium to a similar level as 2.5 μM of wild-type RANTES, although at a much slower rate (FIG. 11).

It appears that at a certain threshold level the disaggregated RANTES mutant will induce a calcium influx by means of the tyrosine kinase pathway; however, the disaggregated mutant E66>S (shown to be essentially dimeric) appears to be at least 200-fold less potent than wild-type RANTES on the TK pathway. This is a surprising and substantial difference in the activity of the disaggregated variants which improves its GPCR selectivity while reducing its pro-inflammatory properties.

Neither wild-type LD78 (hMIP-1α) nor wild-type ACT-2 (hMIP-1β) which are both aggregating chemokines were found to induce calcium mobilisation on Jurkat cells. This phenomenon is therefore RANTES specific.

EXAMPLE 4

Induction of T-cell cell surface marker expression by hRANTES and disaggregated hRANTES mutants.

In addition to calcium mobilisation, a number of other systems are induced following T-cell activation, and can thus be used to measure or demonstrate T-cell activation. CD69, CD11*b* and CD11*c* are examples of cell surface proteins whose expression is elevated on the surface of activated T-cells.

CD69 is a cell surface marker expressed by T-cells early during their activation. CD11*b* (also known as Mac-1) and CD11*c* (also known as gp150, 95) are members of the integrin family of proteins. These molecules are a family of cell surface expressed adhesion molecules that play a part in leukocyte migration, homing and cell-cell interactions. Szabo et al. (Eur. J. Immunol 27,1061–1068, 1997) and Conklyn et al. Cytokine 8, 762–766,1996) demonstrated that the expression of various integrins changed in the presence of chemokines. CD11*b* binds to ICAMs and iC3*b,* and CD11*c* binds to iC3*b* molecules present on the surface of many cells such as lymphocytes, antigen-presenting cells and endothelial cells. Induction of CD11*b* and CD11*c* expression are features linked to the TK pathway, appearing to be part of the T cell activation process. These molecules can therefore be considered markers of T cell activation.

Method

Cultured T lymphocytes were prepared by adding PHA (Sigma) at 5 μg/ml final concentration and interleukin-2 (IL-2, 1:100 dilution of lymphocult-T-HP-prep, Biotest) to a mononuclear cell population ($10^6$ cells/ml suspended in RPMI -1640 medium containing 2 mM glutamine and 10% (vol/vol) fetal calf serum (FCS). After 2 days of incubation at 37° C., the cells were centrifuged and resuspended in fresh medium with IL-2 (same conc.). Every 2–3 days the cells were resuspended in fresh medium supplied with IL-2, keeping the cells at a concentration of about $10^5$ cells/ml.

Cultured T lymphocytes (or freshly purified mononuclear cells, freshly purified T-cells, or Jurkat cells which all gave the same results) were suspended at about $10^6$ cells in 500 μl total volume of FCS free RPMI 1640. They were treated with different concentrations of chemokines (Wild type RANTES, disaggregated RANTES, hMIP-1α or hMIP-1β) or left untreated (addition of PBS only) and incubated for 5 to 7 hours at 37° C. The cells were then spun down, resuspended in PBS (100 μl) and incubated with different monoclonal antibodies. The monoclonal antibodies used were anti-human CD69 (LEU-23-FITC or PE), CD11b (Mac-I-PE) and CD11c (gp-150,95-PE), purchased from Becton Dickinson. The cells were washed and resuspended in PBS, and then analysed by flow cytometry on a Becton Dickinson FACScalibur. The results show the mean fluorescence peak for each monoclonal antibody (FIGS. 12 to 14 and table 2 below).

Wild-type RANTES at 5 μM induced expression of CD69, CD11b and CD11c in cultured human T-lymphocytes. The disaggregated RANTES mutant E66>S (at 5 μM) was incapable of inducing expression of these proteins.

TABLE 2

| Cell surface marker | % of cells expressing the cell surface marker | | |
| --- | --- | --- | --- |
| | Control (PBS) | Wild-type hRANTES | Disaggregated hRANTES E66>S |
| CD69 | 4.71 | 99.06 | 5.61 |
| CD11b | 16.50 | 81.33 | 15.60 |
| CD11c | 0.44 | 99.07 | 0.39 |

These data confirm that wild-type RANTES, but not the disaggregated mutants thereof, activate T-celos and induce the expression of cell-surface proteins associated with T-cel. adhesion. Wild type LD78 (hMIP-I1α) and wild type ACT-2 (hMIP-1β) did not trigger any CD11c expression on T-cells in culture (data not shown).

EXAMPLE 5

T cell activation by HRANTES is inhibited by co-administration of a disaggregated hRANTES mutant.

The antagonist activity of disaggregated hRANTES on the activation of T lymphocytes was demonstrated by the ability of hRANTES E66>S to antagonise hRANTES induced expression of CD11c.

At 20 μM hRANTES E66>S had no effect on CD11c expression, whereas at 5 μM wild-type RANTES CD-I c expression was maximally elevated. The addition of 20 μM E66>S mutant RANTES to the 5 μM wild-type RANTES however, resulted in much reduced level of CD11c expression suggesting that the disaggregated RANTES mutant competes with wild-type RANTES, thus demonstrating an antagonist effect on T-cell activation. FIG. 15 demonstrates the intermediate level of CD11c expression (indicative of T-cell activation) from co-administration of wild-type and mutant RANTES, alongside wild-type and E66>S mutant RANTES administered separately. This provides further evidence that T-cell activation is linked to the aggregation state of RANTES.

EXAMPLE 6

Wild-type hRANTES but not disaggregated hRANTES induces apoptosis in proliferating Jurkat cells.

CD3+ Jurkat cells are immortalised cells and thus continuously proliferate. When their antigen receptors are cross-linked however, they stop growing. Anti-CD3 antibodies and PHA are known to inhibit CD3+ Jurkat cell proliferation and induce apoptosis.

CD3+ Jurkat cells were suspended in FCS free RPMI 1640 on 96 well round bottomed plates, at the density of $2.5 \times 10^4$ cells per well. They were incubated for 40 hours at 37° C. in the presence of different concentrations of chemokines or PHA (Sigma). The plates were then pulsed with $^3$H-thymidine (Amersham) at 1 μCi/well for 4 hours. They were then harvested on a Tomtec 96 well plate harvester and counted on a 1450 microbeta counter (Wallac).

The results are shown in FIG. 16. In the presence of 1 μM of wild-type RANTES, Jurkat cell proliferation was inhibited leading to apoptosis, whereas at the same concentration of disaggregated mutant RANTES the cells continued to proliferate and incorporate radioactive label. The concentration at which wild-type RANTES is able to activate cells via the TK pathway (i.e. approximately 1 μM) is the same concentration at which cell proliferation is inhibited.

This example demonstrates that when hRANTES activates T-cells it affects their proliferative potential as determined by the incorporation of tritiated thymidine into DNA. Bacon et al. (1995, ibid), showed that hRANTES could induce the proliferation of IL-2 dependent T-cell lines. Here it is shown that hRANTES induces activation-induced cell death (AICD) of the IL-2 independent CD3+ Jurkat cell-line. This phenomenon is identical to the well-documented anti-CD3 antibody-induced AICD in Jurkats and is due to the T cell receiving the first activation signal (via the TCR) without the second signal via CD28 usually supplied by antigen presenting cells (APCs). Disaggregated hRANTES analogues and particularly dimeric hRANTES E66>S however, had no effect on the Jurkat cell-line proliferation. These data demonstrate clear differences in the biological activity of disaggregated hRANTES analogues compared to wild-type hRANTES, and suggests a possible role for the disaggregated RANTES analogues as adjuvants.

EXAMPLE 7

Mammalian cells lacking chemokine receptors express hRANTES binding sites.

Analysis of the hRANTES binding properties on human embryonic kidney cells (HEK293; obtained from ECACC; Cat. No.85120602) or chinese hamster ovary cells (CHO) surprisingly showed that these cell lines, which are not known to express RANTES receptors, bound a high proportion of hRANTES. This example demonstrates that hRANTES binding to untransfected mammalian cells, which do not knowingly express functional chemokine receptors, is targeted towards cell-surface proteoglycans. Furthermore, the disaggregated hRANTES analogues were superior at displacing the "non-specific" binding of $^{125}$I-hRANTES than hRANTES.

HEK293 cells ($6 \times 10^5$ cells/well) were incubated with $^{125}$I-hRANTES (0.05 nM final concentration, obtained from Amersham International) in 50 mM TrisHCl pH7.4, in a final volume of 250 μl for 90 minutes at 37° C. The cells were harvested onto Whatman GFB filters (pre-soaked in 0.3% PEI) on a Brandel harvester and washed with 5×1 ml of ice-cold wash buffer (50 mM Tris-HCl, 0.5 M NaCl, 5 mM $MgCl_2$, 1 mM $CaCl_2$, 0.05% BSA, pH7.4). Filters were counted for 2 minutes on a Beckman Cobra counter. About 1700cpm of $^{125}$I-hRANTES bound to the HEK293 cell-line. This was not displaced by the addition of excess cold hRANTES. At 3000 nM of wt hRANTES the number of counts bound increased probably due to aggregation of the ligands. This phenomenon has been observed by others and discussed in the art eg. Neote et al. (ibid). RANTES E66>S at 3000 nM reduced the number of counts bound to about 590cpm. Thus disaggregated RANTES analogues appear to be better than hRANTES at displacing $^{125}$I-hRANTES bound to HEK293 cells.

The same method was used to compare the binding of $^{125}$I-hRANTES (0.125 nM) or $^{125}$I-hRANTES E66>S (0.2 nM) to normal chinese hamster ovary cells (CHO) or to a proteoglycan deficient CHO cell-line pgsA-745 (pgsA-745 or GAG-ve) ($5 \times 10^5$ cells/well). The CHO cells and the pgsA-745 cell-line w ere obtained from ECACC (catalogue numbers 85050302) and ATOC (CRL-2242) respectively. Both cell lines were cultured in Ham's F12 medium (Gibco cat no.21765) with the addition of 10% v/v fetal calf serum.

$^{125}$I-hRANTES bound to CHO cells (about 5730cpm total counts) and was displaced by hRANTES E66>S at 3000 nM (down to 4000cpm) therefore 30% of the counts were displaceable. $^{125}$I-hRANTES bound to pgsA-745 cells (about 3110cpm total counts) and was displaced by hRANTES E66>S at 3000nM (down to 2260cpm) therefore 27% of the counts were displaceable. These results showed that $^{125}$I-hRANTES had a relatively poor affinity for CHO cells.

$^{125}$I-hRANTES E66>S bound to CHO cells (about 18300cpm total counts) which were displaced by hRANTES E66>S at 3000 nM (down to 4760cpm) therefore 74% of the counts were displaceable. $^{125}$I-hRANTES E66>S bound relatively poorly to pgsA-745 cells (about 5080cpm total counts) and little was displaced by hRANTES E66>S at 3000 nM (down to 2840cpm) therefore 44% of the counts were displaceable. These results showed that $^{125}$I-hRANTES E66>S had a much greater affinity for the binding sites on CHO cells than $^{125}$I-hRANTES and that hRANTES E66>S was more able to displace bound counts than hRANTES. Furthermore, there was a substantial reduction in the quantity of total binding and in the proportion of binding which was non-displaceable when the pgsA-745 cells were used. This indicated that the binding site was probably a proteoglycan.

The pgsA-745 cell-line appears to be substantially free from background $^{125}$I-hRANTES E66>S binding, and the apparent increased affinity of hRANTES E66>S for the proteoglycan binding site indicates its potential use in the development of a screen to detect chemicals which block the chemokine-proteoglycan interaction.

EXAMPLE 8

Disaggregated hRANTES analogues retain HIV inhibitory activity;Assessing the ability of the Glu26>Ala (E26>A) disaggregated mutant of hRANTES to inhibit HIV replication.

3 day old CD8 depleted IL-2 and phytohaemagglutinin (PHA) stimulated peripheral blood mononuclear cells (PBMCs) from a healthy donor were washed x 3 in RPMI -1640 (LifeTech.) and infected with a non-syncytium inducing HIV-1 clinical isolate (HIV-1$^{RR}$) for 1 hour at room temperature with frequent mixing. The cells were then washed ×3 in RPMI-1640 and grown in the presence or absence (controls) of varying concentrations of the disaggregated hRANTES mutant E26>A with rIL-2 (Cetus Corp.) at a concentration of 10 U/ml and incubated at 370° C. for 4 days. After this period the medium was discarded without disturbing the cells and fresh E26>A with IL-2 was added. This was incubated for a further 3 days at 37° C. The supernatant fluid was assessed for the presence of p24 viral core antigen using a commercially available p24 ELISA kit (Coulter).

TABLE 3

| hRANTES E26>A (pg/ml) | Well 1 p24 pg/ml | Well 2 p24 pg/ml | Mean p24 pg/ml | % Control No hRANTES E26>A |
|---|---|---|---|---|
| 0.03 | 1054 | 1436 | 1245 | 83 |
| 0.1 | 1225 | 1104 | 1164 | 78 |
| 0.3 | 265 | 435 | 350 | 23 |
| 1.0 | 91 | 0 | 46 | 3 |
| 3.0 | 0 | 0 | 0 | 0 |
| 10.0 | 0 | 0 | 0 | 0 |

The results of this assay may be seen graphically in FIG. 17. In this assay the disaggregated hRANTES mutant E26>A had an $IC_{50}$ value of 28 nM which is approximately 0.22 μg/ml. These results are typical of three repeated experiments. This example demonstrates that hRANTES E26>A retains the ability to inhibit the infection of peripheral blood mononuclear cells by a clinical isolate of HIV-1.

EXAMPLE 7b

Assessing the ability of the disaggregated hRANTES mutants to inhibit HIV replication.

This example was a more extensive study of the HIV inhibitory activity of hRANTES, comparing the activities of hRANTES E26>A, hRANTES E66>S and hRANTES E26>A E66>S with wild-type hRANTES. Two HIV-1 viruses were also used AT-5 and SF162. The SF162 isolate is available from the NIH under the AIDS research and reference reagent Program, Cat. No. 276. Alternative monocytotropic HIV-1 isolates would however, be expected to give similar results. The AT-5 virus is less aggressive and therefore more easily suppressed than the SF162 viral isolate. The multiplicity of infection is also a key component of these assays as the addition of too much virus would swamp the inhibitory activity of hRANTES or its analogues. To standardise the level of input virus the titre of the virus stocks was determined and the quantity of virus required to infect 50% of a culture determined ($TCID_{50}$). Two multiplicities of infection were used in the study 20× and 100× the $TCID_{50}$ for each virus. Both viruses were propagated and titered in primary PHA activated peripheral blood mononuclear cells (PBMC).

To perform the assay, PBMC (3 days post-PHA activation) were washed, resuspended at $10^6$/ml (0.1 ml/well of a 96-well plate) and incubated for 2 hours with various concentrations of hRANTES or its analogues (0.05 ml/well of a 96-well plate). Virus (20× or 100× $TCID_{50}$/0.05 ml) was added to each well plus or minus chemokine (also to wells with no PBMC to control for soluble p24 antigen levels) and incubated at 37° C. overnight. The PBMC were washed twice by centrifugation and fed fresh medium (10% FCS/ RPMI/IL-2 5 I.U./ml) containing the appropriate concentration of hRANTES or its analogue under test. The plates were incubated for 5 days at 37° C. and the extracellular fluid harvested and tested for the presence of viral p24 antigen by EIA (assay sensitivity of 10 pg/0.05ml). The $IC_{50}$ values were determined by the percentage reduction of p24 in the test wells.

TABLE 4

WT hRANTES.

| Virus & | OD-490 nm value measuring p24 antigen production [pg/50 ul] in presence of: | | | |
|---|---|---|---|---|
| Dose | no agent | 200 ng/ml | 400 ng/ml | 800 ng/ml |
| AT-5 100 | 0.74 [37 pg] | 0.09 | 0.05 | 0.04 |
| AT-5 20 | 0.68 [34 pg] | 0.05 | 0.06 | 0.04 |
| SF162 100 | 0.87 [50 pg] | 0.05 | 0.04 | 0.04 |
| SF162 20 | 0.78 [40 pg] | 0.03 | 0.05 | 0.03 |

TABLE 5

E26>A.

| Virus & | OD-490 nm value measuring p24 antigen production [pg/50 μl] presence of: | | | |
|---|---|---|---|---|
| Dose | no agent | 200 ng/ml | 400 ng/ml | 800 ng/ml |
| AT-5 100 | 0.62 [30 pg] | 0.16 [6 pg] | 0.05 | 0.03 |
| AT-5 20 | 0.56 [24 pg] | 0.03 | 0.04 | 0.04 |
| SF162 100 | 0.78 [40 pg] | 0.67 [34 pg] | 0.43 [18 pg] | 0.04 |
| SF162 20 | 0.75 [37 pg] | 0.06 | 0.05 | 0.03 |

TABLE 6

E66>S.

| Virus & | OD-490 nm value measuring p24 antigen production [pg/50 μl] in presence of: | | | |
|---|---|---|---|---|
| Dose | no agent | 200 ng/ml | 400 ng/ml | 800 ng/ml |
| AT-5 100 | 0.63 [30 pg] | 0.12 [4.5 pg] | 0.05 | 0.03 |
| AT-5 20 | 0.68 [32 pg] | 0.04 | 0.03 | 0.04 |
| SF162 100 | 0.76 [38 pg] | 0.26 [11 pg] | 0.03 | 0.04 |
| SF162 20 | 0.63 [30 pg] | 0.08 | 0.05 | 0.03 |

TABLE 7

E26>A + E66>S.

| Virus & | OD-490 nm value measuring p24 antigen production [pg/50 μl] in presence of: | | | |
|---|---|---|---|---|
| Dose | no agent | 200 ng/ml | 400 ng/ml | 800 ng/ml |
| AT-5 100 | 0.68 [32 pg] | 0.18 [8 pg] | 0.07 | 0.04 |
| AT-5 20 | 0.63 [30 pg] | 0.11 [5 pg] | 0.07 | 0.02 |
| SF162 100 | 0.85 [50 pg] | 0.86 [50 pg] | 0.49 [20 pg] | 0.25 [11 pg] |
| SF162 20 | 0.69 [32 pg] | 0.03 | 0.05 | 0.05 |

This data demonstrates that wild-type HRANTES and the disaggregated hRANTES analogues are capable of inhibiting/neutralising HIV-1 infection (both AT-5 and the more aggressive SF162 virus) and that disaggregated HRANTES analogues are of comparable potency to the wild-type molecule.

What is claimed is:

1. A disaggregated mutant human RANTES chemokine molecule wherein the glutamic acid residue at position 26 of wild-type hRANTES, said wild-type hRANTES comprising the amino acid sequence set forth in SEQ ID NO: 1 is substituted by an alanine residue.

2. A disaggregated mutant human RANTES chemokine molecule wherein the glutamic acid residue at position 66 of wild-type RANTES, said wild-type hRANTES comprising the amino acid sequence set forth in SEQ ID NO:1. is substituted by a serine residue.

3. A disaggregated mutant human RANTES chemokine molecule wherein one or both of the residues at position 26 and 66 of wild-type hRANTES said wild-type hRANTES comprising the amino acid sequence set forth in SEQ ID NO: 1, is substituted by other amino acids, and wherein the mutant is incapable at physiological ionic strengh of forming a stable multimner greater than a dodecamer as determined by Sedimentation Equilibrium Analytical Ultracentrifugation (AUC).

4. A disaggregated mutant human RANTES chemokine molecule wherein the residues at positions 26 and 66 of wild-type hRANTES, said wild-type hRANTES comprising the amino acid sequence set forth in SEQ ID NO:1are substituted by alanine and serine, respectively.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:1:

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
                35                  40                  45

Val Cys Ala Asn Pro Glu Lys Lys Trp Val Arg Glu Tyr Ile Asn Ser
    50                  55                  60

Leu Glu Met Ser
65

(2) INFORMATION FOR SEQ ID NO:2:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

AGCTTGGATA AAAGATCTCC ATATTCTTCA GACACCACAC CTTGCTGT        48

(2) INFORMATION FOR SEQ ID NO:3:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

AAGCAAAACA GCAAGGTGTG GTGTCTGAAG AATATGGAGA TCTTTTATCC A      51

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:4:

TTTGCTTACA TTGCTAGGCC TTTGCCTCGT GCCCACATCA AG        42

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

AATATTCCTT GATGTGGGCA CGAGGCAAAG GCCTAGCAAT GT        42

(2) INFORMATION FOR SEQ ID NO:6:

(i) SEQUENCE CHARACTERISTICS:

(A) LENGTH: 49 base pairs
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:6:

GAATATTTCT ACACTTCTGG TAAGTGCTCC AACCCTGCAG TTGTCTTTG                49

(2) INFORMATION FOR SEQ ID NO:7:

(i) SEQUENCE CHARACTERISTICS:
(A) LENGTH: 49 base pairs
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:7:

CTGGTCACAA AGACAACTGC AGGGTTGGAG CACTTACCAG AAGTGTAGA                49

(2) INFORMATION FOR SEQ ID NO:8:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:8:

TGACCAGAAA GAACCGTCAA GTTTGTGCCA ACCCAGAGAA GAAATGG                  47

(2) INFORMATION FOR SEQ ID NO:9:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:9:

CTCTAACCCA TTTCTTCTCT GGGTTGGCAC AAACTTGACG GTTCTTT                  47

(2) INFORMATION FOR SEQ ID NO:10:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:10:

GTTAGAGAAT ACATTAACTC TTTGGAGATG TCCTAATAAG                          40

(2) INFORMATION FOR SEQ ID NO:11:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:11:

GATCCTTATT AGGACATCTC CAAAGAGTTA ATGTATT                             37

(2) INFORMATION FOR SEQ ID NO:12:

(i) SEQUENCE CHARACTERISTICS:
            (A) LENGTH: 232 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:12:

AAGCTTGGAT AAAAGATCCC CATATTCTTC AGACACCACA CCTTGCTGTT TTGCTTACAT    60

TGCCAGACCA TTGCCTCGTG CCCACATCAA GGAATATTTC TACACTTCTG GTAAGTGCTC   120

CAACCCAGCA GTTGTCTTTG TGACCAGAAA GAACCGTCAA GTTTGTGCCA ACCCAGAGAA   180

GAAATGGGTT AGAGAATACA TTAACTCTTT GGAGATGTCC TAATAAGGAT CC           232

(2) INFORMATION FOR SEQ ID NO:13:

(i) SEQUENCE CHARACTERISTICS:
            (A) LENGTH: 73 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:13:

Ser Leu Asp Lys Arg Ser Pro Tyr Ser Ser Asp Thr Thr Pro Cys Cys
1               5                   10                  15

Phe Ala Tyr Ile Ala Arg Pro Leu Pro Arg Ala His Ile Lys Glu Tyr
                20                  25                  30

Phe Tyr Thr Ser Gly Lys Cys Ser Asn Pro Ala Val Val Phe Val Thr
            35                  40                  45

```
Arg Lys Asn Arg Gln Val Cys Ala Asn Pro Glu Lys Lys Trp Val Arg
     50                  55                  60

Glu Tyr Ile Asn Ser Leu Glu Met Ser
 65                  70
```

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:14:

```
GTGTAGAAAT AAGCCTTGAT GTGG                                         24
```

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:15:

```
CCTTATTAGG ACATTGACAA GGAGTTAATG                                   30
```

(2) INFORMATION FOR SEQ ID NO:16:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:16:

```
Ser Pro Tyr Ser Ser Asp Thr Thr Pro Cys Cys Phe Ala Tyr Ile Ala
 1               5                  10                  15

Arg Pro Leu Pro Arg Ala His Ile Lys Ala Tyr Phe Tyr Thr Ser Gly
             20                  25                  30

Lys Cys Ser Asn Pro Ala Val Val Phe Val Thr Arg Lys Asn Arg Gln
             35                  40                  45

Val Cys Ala Asn Pro Glu Lys Lys Trp Val Arg Glu Tyr Ile Asn Ser
     50                  55                  60

Leu Glu Met Ser
 65
```

(2) INFORMATION FOR SEQ ID NO:17:

-continued

```
     (i) SEQUENCE CHARACTERISTICS:
          (A) LENGTH: 68 amino acids
          (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:17:

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Ser Met Ser
65

(2) INFORMATION FOR SEQ ID NO:18:

(i) SEQUENCE CHARACTERISTICS:
          (A) LENGTH: 68 amino acids
          (B) TYPE: amino acid
          (C) STRANDEDNESS: single
          (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:18:

Ser Pro Tyr Ser Ser Asp Thr Thr Pro Cys Cys Phe Ala Tyr Ile Ala
1               5                   10                  15

Arg Pro Leu Pro Arg Ala His Ile Lys Ala Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Ser Met Ser
65
```